(12) United States Patent
De Bruyker et al.

(10) Patent No.: US 10,379,074 B2
(45) Date of Patent: Aug. 13, 2019

(54) SYSTEM AND METHOD FOR SHIELDED CHEMICAL SENSING USING A FINE-LINE SHIELDED SENSING STRUCTURE

(71) Applicant: Neotek Energy, Inc., Plano, TX (US)

(72) Inventors: Dirk De Bruyker, San Jose, CA (US);
Richard C. Eden, Briarcliff, TX (US);
Daniel O'Brien, Sunnyvale, CA (US)

(73) Assignee: NeoTek Energy, Inc., Plano, TX (US)

( * ) Notice: Subject to any disclaimer, the term of this patent is extended or adjusted under 35 U.S.C. 154(b) by 110 days.

(21) Appl. No.: 15/851,465

(22) Filed: Dec. 21, 2017

(65) Prior Publication Data
US 2019/0195822 A1      Jun. 27, 2019

(51) Int. Cl.
*G01N 27/26*      (2006.01)
*G01N 27/22*      (2006.01)

(52) U.S. Cl.
CPC ........... *G01N 27/26* (2013.01); *G01N 27/228* (2013.01)

(58) Field of Classification Search
CPC ...... G01N 27/26; G01N 27/228; G01N 27/24; G01N 27/00
USPC .................................. 324/661, 658, 649, 600
See application file for complete search history.

(56) References Cited

U.S. PATENT DOCUMENTS

| | | |
|---|---|---|
| 4,728,882 A | 3/1988 | Stanbro et al. |
| 6,781,388 B2 | 8/2004 | Wang et al. |
| 6,842,018 B2 | 1/2005 | McIntosh |
| 7,837,844 B2 | 11/2010 | Patel et al. |
| 8,193,821 B2 | 6/2012 | Mueller et al. |
| 2012/0240752 A1* | 9/2012 | Matsuoka ............ G10H 3/185 84/731 |
| 2014/0291778 A1 | 10/2014 | Vaiana et al. |
| 2015/0268795 A1* | 9/2015 | Kurasawa ............ G06F 3/0418 345/174 |
| 2017/0349430 A1* | 12/2017 | Sato ........................ G01L 9/005 |

* cited by examiner

*Primary Examiner* — Giovanni Astacio-Oquendo

(57) ABSTRACT

A sensor apparatus includes a substrate, a plurality of parallel interdigitated sensor electrode fingers disposed over the substrate, a peripheral shield disposed over at least some of a periphery of the substrate, and a sensing material disposed in gaps formed by surfaces of the sensor electrode fingers and the peripheral shield. In some embodiments, an area shield is also disposed over the electrode fingers.

20 Claims, 39 Drawing Sheets

| CAPACITANCE MATRIX VALUES CONVERTED TO C/A, CAPACITANCE PER SQUARE CM OF SENSOR AREA. ALL VALUES ARE IN pF/cm^2: (NOMINAL SENSOR AREA IS 0.13297 cm^2) | | | | | | | | |
|---|---|---|---|---|---|---|---|---|
| 5.0μm SiN OVER 0.3μm M1 FINGERS CONDUCTIVE FLUID (ELECTRODE "C") | | | | INSULATING WATER (Er=80) | | | INSULATING GAS (Er=1.00) | |
|  | C | B | A |  | B | A | B | A |
| C | 1027.9568 | -513.94932 | -514.00747 | B | 1978.2722 | -1978.2722 | 1977.6539 | -1977.6539 |
| B | -513.88634 | 2235.4174 | -1721.5274 | A | -1978.2722 | 1978.2722 | -1977.6539 | 1977.6539 |
| A | -514.00747 | -1721.5274 | 2235.5348 |  |  |  |  |  |
| CABG | 1721.5274 | pF/cm^2 |  | CAB | 1978.2722 | pF/cm^2 | 1978.501 | pF/cm^2 |
| ΔC=CABO-CBG | 256.97357 | FLUID GROUNDED 12.9883% |  |  |  |  |  |  |
| CABO | 1978.501 | pF/cm^2 | FLUID FLOATING |  |  |  |  |  |
| 2.0μm SiN OVER 0.3μm M1 FINGERS CONDUCTIVE FLUID (ELECTRODE "C") | | | | INSULATING WATER (Er=80) | | | INSULATING GAS (Er=1.00) | |
|  | C | B | A |  | B | A | B | A |
| C | 2448.7048 | -1224.4143 | -1224.2905 | B | 2020.6648 | -2020.6648 | 1940.1253 | -1940.1253 |
| B | -1224.3826 | 2646.8376 | -1422.4549 | A | -2020.6648 | 2020.6648 | -1940.1253 | 1940.1253 |
| A | -1224.2905 | -1422.4549 | 2646.7451 |  |  |  |  |  |
| CABG | 1422.4549 | pF/cm^2 |  | CAB | 2020.6648 | pF/cm^2 | 1940.1253 | pF/cm^2 |
| ΔC=CABO-CBG | 612.16828 | FLUID GROUNDED 30.0876% |  |  |  |  |  |  |
| CABO | 2034.6232 | pF/cm^2 | FLUID FLOATING |  |  |  |  |  |

FIG. 3D

UN-SHIELDED INTERDIGITATED SENSOR ARRAY CAPACITANCE MODEL

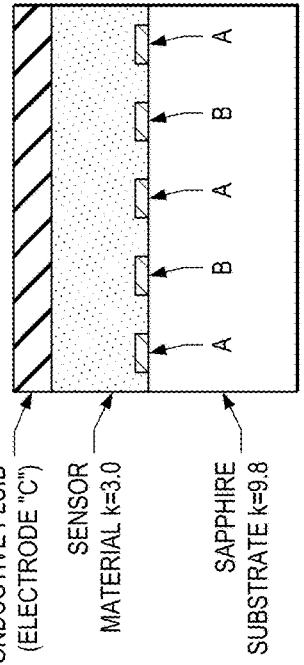

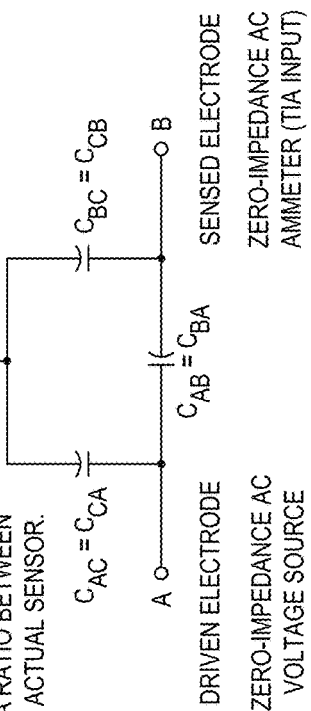

- CONDUCTIVE FLUID (ELECTRODE "C")
- SENSOR MATERIAL k=3.0
- SAPPHIRE SUBSTRATE k=9.8

CAPACITANCE MATRIX IS DEFINED ASSUMING ALL ELECTRODES HAVE ZERO IMPEDANCE TO GROUND (UN-USED ELECTRODES GROUNDED). CAPACITANCE MATRIX VALUES COME DIRECTLY FROM 2-D FIELDS SIMULATIONS, SCALED BY AREA RATIO BETWEEN SIMULATION AND ACTUAL SENSOR.

IMPEDANCE TO GROUND TYPICALLY VARIES FROM SHORT (GROUNDED FLUID CASE) TO LOW CAPACITANCE OPEN (FLOATING FLUID CASE)

CONDUCTIVE FLUID

DRIVEN ELECTRODE — ZERO-IMPEDANCE AC VOLTAGE SOURCE

SENSED ELECTRODE — ZERO-IMPEDANCE AC AMMETER (TIA INPUT)

$C_{AC} = C_{CA}$
$C_{AB} = C_{BA}$
$C_{BC} = C_{CB}$

GROUNDED (SHORTED) FLUID CASE:
$C_{ABG} = C_{AB}$

FLOATING (OPEN) FLUID GENERAL CASE:
$C_{ABO} = C_{AB} + 1/[(1/C_{AC}) + (1/C_{BC})] = C_{AB} + C_{AC}/[1 + (C_{AC}/C_{BC})]$

GENERAL CASE; WITH OR WITHOUT ELECTRODE SYMMETRY

FLOATING (OPEN) FLUID SPECIAL CASE WITH SYMMETRICAL ELECTRODES:
$C_{ABO} = C_{AB} + C_{AC}/2 = C_{AB} + C_{CC}/4$ FOR $C_{BC} = C_{AC}$

SYMMETRICAL ELECTRODE SPECIAL CASE; EQUAL WIDTH OF "A" AND "B" FINGERS AND EQUAL GAPS

| 3.0μm POST HEIGHT, x=7.0μm | | | | |
|---|---|---|---|---|
| 7.0μm SENSOR MATERIAL OVER 3.0μm HIGH x 1μm WIDE POSTS WITH 2.0μm | | | | |
| CONDUCTIVE FLUID (ELECTRODE "C") | | | | |
|  | C | G | B | A |
| C | 321.453113 | -316.22445 | -20.243358 | -20.24713 |
| G | -316.21287 | 1512.56663 | -508.31317 | -508.33771 |
| B | -20.256606 | -598.34907 | 2062.67905 | -1434.0764 |
| A | -20.24713 | -598.3371 | -5434.0764 | 2062.66336 |
| M1 FINGERS "B" SENSED | | | | |
| CABG | 1434.07642 | pF/cm^2 |  | FLUID GROUNDED |
| ΔC=CABO-CBG | 1.14970647 |  |  | 0.0802% CHANGE |
| CABO | 1435.22812 | pF/cm^2 |  | FLUID FLOATING |

| 3.0μm POST HEIGHT, x=7.0μm | | | k=2.70 SENSOR MATERIAL | |
|---|---|---|---|---|
| 7.0μm k=2.70 SENSOR MATERIAL OVER 4.0μm HIGH x 1μm WIDE POSTS WITH | | | | |
| CONDUCTIVE FLUID (ELECTRODE "C") | | | | |
|  | C | G | B | A |
| C | 321.453113 | -265.15473 | -18.14558 | -15.15282 |
| G | -265.14574 | 1435.88204 | -575.36271 | -575.34129 |
| B | -18.148329 | -575.44425 | 1002.25167 | -1306.661 |
| A | -18.15282 | -575.34129 | -1398.661 | 1992.15492 |
| M1 FINGERS "B" SENSED | | | | |
| CABG | 1398.66096 | pF/cm^2 |  | FLUID GROUNDED |
| ΔC=CABO-CBG | 1.00487644 |  |  | 0.0733% CHANGE |
| CABO | 1399.68583 | pF/cm^2 |  | FLUID FLOATING |

| CHANGE IN CAPACITANCE MATRIX FROM k=3.00 TO k=2.70 SENSOR MATERIAL | | | | |
|---|---|---|---|---|
|  | C | G | B | A |
| C | 35.2618375 | -31.069717 | -2.0977779 | -2.09431 |
| G | -31.067129 | 77.0145833 | -22.950458 | -22.006417 |
| B | -2.1072771 | -22.905417 | 60.4277917 | -35.417458 |
| A | -2.09631 | -22.905417 | -35.417458 | 60.5064583 |

| % CHANGE IN CAPACITANCE MATRIX FROM 10% CHANGE (k=3.00 TO k=2.70) | | | | |
|---|---|---|---|---|
|  | C | G | B | A |
| C | 9.885% | 9.825% | 10.363% | 10.344% |
| G | 9.825% | 5.091% | 3.836% | 3.843% |
| B | 10.400% | 3.828% | 2.944% | 2.470% |
| A | 10.344% | 3.843% | 2.470% | 2.948% |

| x 0.5μm M1 FINGERS | | | | |
|---|---|---|---|---|
| | INSULATING WATER (Er=80) | | | |
| | | G | B | A |
| | G | 1256.453 | -644.61604 | -641.83696 |
| | B | -616.80296 | 2052.54458 | -1436.0363 |
| | A | -641.83696 | -1436.0363 | 2077.87333 |
| | | | | |
| | SHIELD "G" SENSED | | | |
| | CAGG | 598.337708 | pF/cm^2 | FLUID GROUNDED |
| | ΔC=CAGO-CAGG | 17.9482328 | | 2.9997% CHANGE |
| | CAGO | 616.285541 | pF/cm^2 | FLUID FLOATING |
| | | | | |
| 2.0μm x 0.5μm M1 FINGERS | | | | |
| | INSULATING WATER (Er=80) | | | |
| | | G | B | A |
| | G | | | |
| | B | | | |
| | A | | | |
| | | | | |
| | SHIELD "G" SENSED | | | |
| | CAGG | 575.341292 | pF/cm^2 | FLUID GROUNDED |
| | ΔC=CAGO-CAGG | 16.1025014 | | 2.7988% CHANGE |
| | CAGO | 591.443793 | pF/cm^2 | FLUID FLOATING |
| (10% CHANGE) | | | | |
| | M1 FINGERS "B" SENSED | | SHIELD "G" SENSED | |
| | sΔ/(CABG) | 35.41746 | pF/cm^2 | sΔ/CAGG |
| | sΔ/(CABO) | 35.5422874 | pF/cm^2 | sΔ/CAGO |
| | sΔ/ΔCABG | 34.55778 | "SNR" | sΔ/ΔCAGG |
| | sΔ/ΔCABO | 34.6795828 | "SNR" | sΔ/ΔCAGO |
| SENSOR MATERIAL | | | | |
| | | | | |
| | | | | |
| | 24.697% | =ELECTROSTATIC SENSING EFFICIENCY (*%Δ | | |
| ESTIMATED | 15% | =ELECTROSTATIC SENSING EFFICIENCY (*%Δ | | |

FIG. 11C

| | | | INSULATING GAS (Er=1.00) | | |
|---|---|---|---|---|---|
| | | | G | B | A |
| | | G | 1232.51946 | -616.29179 | -616.22767 |
| | | B | -616.27046 | 2051.47704 | -1435.2067 |
| | | A | -616.22767 | -1435.2087 | 2051.43629 |
| | | | | | |
| | | BOTH "B" AND "G" SENSED | | | |
| | | CABG-CAGG | 2032.41613 | pF/cm^2 | FLUID GROUNDED |
| | | ΔC=CAGO-CAGG | 19.0979383 | | 0.9397% |
| | | CABO-CAGO | 2051.51406 | pF/cm^2 | FLUID FLOATING |
| | | | | | |
| | | INSULATING GAS (Er=1.00) | | | |
| | | | G | B | A |
| | | G | | | |
| | | B | | | |
| | | A | | | |
| | | | | | |
| | | BOTH "B" AND "G" SENSED | | | |
| | | CABG-CAGG | 1974.00225 | pF/cm^2 | FLUID GROUNDED |
| | | ΔC=CAGO-CAGG | 17.1273779 | | 0.8676% |
| | | CABO-CAGO | 1991.12963 | pF/cm^2 | FLUID FLOATING |
| | | | | | |
| | | BOTH "B" AND "G" SENSED | | | |
| 22.99642 | pF/cm^2 | Δ/(CABG-CAGG) | 58.413875 | pF/cm^2 | |
| 24.84215 | pF/cm^2 | Δ/(CABO-CAGO) | 60.3844334 | pF/cm^2 | |
| 1.428127 | "SNR" | Δ/Δ/(CABG+CAGG) | 3.41055563 | "SNR" | |
| 1.542751 | "SNR" | Δ/Δ/(CABO+CAGO) | 3.52560667 | "SNR" | |

FROM FIG. 11B

CAB/%Δk) WITH NO PROTECTION OF "A" AND "B" ELECTRODE
CAB/%Δk) WITH 0.4μm SiN PROTECTION SURROUNDING "A" AND "B" ELECTRODES

| y=4.0μm POST HEIGHT, x=8.0μm, z=3.0μm RIDGE HEIGHT ||||
|---|---|---|---|---|
| 8.0μm SENSOR MATERIAL OVER 4.0μm HIGH x 1.6-1.0μm WIDE POSTS WITH |||||
| CONDUCTIVE FLUID (ELECTRODE "C") |||||
| | C | G | B | A |
| C | 320.20401 | -313.7181 | -3.2573685 | -3.228547 |
| G | -312.71191 | 874.96825 | -280.6069 | -280.65099 |
| B | -3.1864285 | -280.52519 | 1207.3566 | -923.64394 |
| A | -3.220547 | -280.65099 | -923.64394 | 1207.5235 |
| M1 FINGERS "B" SENSED |||||
| CABG | 923.64304 | pF/cm^2 | | FLUID GROUNDED |
| ΔC=CABO-CBG | 0.0321368 | | | 0.003479% CHANGE |
| CABO | 923.67607 | pF/cm^2 | | FLUID FLOATING |
| y=4.0μm POST HEIGHT, x=8.0μm, z=3.0μm RIDGE HEIGHT |||||
| 8.0μm SENSOR MATERIAL OVER 4.0μm HIGH x 1.6-1.0μm WIDE POSTS WITH |||||
| CONDUCTIVE FLUID (ELECTRODE "C") |||||
| | C | G | B | A |
| C | 288.71853 | -283.03776 | -2.8586135 | -2.8221236 |
| G | -283.07616 | 816.47069 | -266.66091 | -266.73159 |
| B | -2.7648308 | -266.66211 | 1129.9088 | -800.49221 |
| A | -2.8221236 | -266.73150 | -660.49221 | 1130.0450 |
| M1 FINGERS "B" SENSED |||||
| CABG | 860.49221 | pF/cm^2 | | FLUID GROUNDED |
| ΔC=CABO-CBG | 0.0270303 | | | 0.003141% CHANGE |
| CABO | 860.51924 | pF/cm^2 | | FLUID FLOATING |
| CHANGE IN CAPACITANCE MATRIX FROM k=3.00 TO k=2.70 SENSOR MATERIAL |||||
| | C | G | B | A |
| C | 31.486488 | -30.680325 | -0.308755 | -0.4064234 |
| G | -30.633738 | 58.497563 | -13.945988 | -13.9194 |
| B | -0.4215978 | -13.673075 | 77.447813 | -63.151725 |
| A | -0.4064234 | -13.9194 | -63.151725 | 77.477625 |
| % CHANGE IN CAPACITANCE MATRIX FROM Δk=-10% CHANGE (k=3.00 TO k= |||||
| | C | G | B | A |
| C | 9.833% | 9.780% | 12.242% | 12.588% |
| G | 9.765% | 6.686% | 4.970% | 4.960% |
| B | 13.231% | 4.945% | 6.415% | 6.837% |
| A | 12.588% | 4.960% | 6.837% | 6.416% |

| | k=3.00 SENSOR MATERIAL | | 1.6μm SHIELD | |
|---|---|---|---|---|
| 2.0μm x 0.5μm M1 FINGERS ON 3.0μm RIDGES (2.5μm SiO2+0.5μm SiN) WITH | | | | |
| | INSULATING WATER (Er=80) | | | |
| | | G | B | A |
| | G | 0 | 0 | 0 |
| | B | 0 | 0 | 0 |
| | A | 0 | 0 | 0 |
| | | | | |
| | SHIELD "G" SENSED | | | |
| | CAGG | 280.65099 | pF/cm^2 | FLUID GROUNDED |
| | ΔC=CAGO-CAGG | 3.1630886 | | 1.1271% CHANGE |
| | CAGO | 283.81408 | pF/cm^2 | FLUID FLOATING |
| | k=2.70 SENSOR MATERIAL | | 1.6μm SHIELD | |
| 2.0μm x 0.5μm M1 FINGERS ON 3.0μm RIDGES (2.5μm SiO2+0.5μm SiN) WITH | | | | |
| | INSULATING WATER (Er=80) | | | |
| | | G | B | A |
| | G | | | |
| | B | | | |
| | A | | | |
| | | | | |
| | SHIELD "G" SENSED | | | |
| | CAGG | 266.73159 | pF/cm^2 | FLUID GROUNDED |
| | ΔC=CAGO-CAGG | 2.7669912 | | 1.0374% CHANGE |
| | CAGO | 269.49858 | pF/cm^2 | FLUID FLOATING |
| (-10% CHANGE IN k) | | | | |
| | M1 FINGERS "B" SENSED | | SHIELD "G" SENSED | |
| | sΔ/CABG | 63.15172 | pF/cm^2 | sΔ/CAGG |
| | sΔ/CABO | 63.154431 | pF/cm^2 | sΔ/CAGO |
| | sΔ/ΔCABG | 2336.334 | "SNR" | sΔ/ΔCAGG |
| | sΔ/ΔCABO | 2336.523 | "SNR" | sΔ/ΔCAGO |
| 2.70) SENSOR MATERIAL | | | | |
| | | | | |
| | | 68.372% | =ELECTROSTATIC SENSING EFFICIENCY (*%Δ | |

FROM FIG. 12A / TO FIG. 12C

FIG. 12B

FROM FIG. 12B

| WIDTH WITH SiN POST TAPERING DOWN TO 1.0μm | | | | | |
|---|---|---|---|---|---|
| 0.1μm SiN PROTECTION AROUND METAL | | | | | |
| | | INSULATING GAS (Er=1.00) | | | |
| | | | G | B | A |
| | | G | 0 | 0 | 0 |
| | | B | 0 | 0 | 0 |
| | | A | 0 | 0 | 0 |
| | | | | | |
| | | BOTH "B" AND "G" SENSED | | | |
| | | CABG-CAGG | 1204.2949 | pF/cm^2 | FLUID GROUNDED |
| | | ΔC=CAGO-CAGG | 3.1952244 | | 0.2653% |
| | | CABO-CAGO | 1207.4901 | pF/cm^2 | FLUID FLOATING |

| WIDTH WITH SiN POST TAPERING DOWN TO 1.0μm | | | | | |
|---|---|---|---|---|---|
| 0.1μm SiN PROTECTION AROUND METAL | | | | | |
| | | INSULATING GAS (Er=1.00) | | | |
| | | | G | B | A |
| | | G | | | |
| | | B | | | |
| | | A | | | |
| | | | | | |
| | | BOTH "B" AND "G" SENSED | | | |
| | | CABG-CAGG | 1127.2238 | pF/cm^2 | FLUID GROUNDED |
| | | ΔC=CAGO-CAGG | 2.7960214 | | 0.2479% |
| | | CABO-CAGO | 1130.0178 | pF/cm^2 | FLUID FLOATING |

| | | BOTH "B" AND "G" SENSED | | | |
|---|---|---|---|---|---|
| 13.9194 | pF/cm^2 | sΔ/(CABG-CAGG) | 77.071125 | pF/cm^2 | |
| 14.3155 | pF/cm^2 | sΔ/(CABO-CAGO) | 77.472328 | pF/cm^2 | |
| 5.030518 | "SNR" | Δ/Δ/(CABG+CAGG) | 27.4843 | "SNR" | |
| 5.173669 | "SNR" | Δ/Δ/(CABO+CAGO) | 27.727803 | "SNR" | |

| CAB/%Δk) WITH 0.1μm SiN PROTECTION SURROUNDING "A" AND "B" ELECTRODES | | | | | |
|---|---|---|---|---|---|

FIG. 12C

| 1μm/1μm FINGERS y=3.0μm POST HEIGHT, x=5.0μm, z=3.0μm RIDGE HEIGHT |||||
|---|---|---|---|---|
| 5.0μm SENSOR MATERIAL OVER 3.0μm HIGH x 1.0μm WIDE POSTS WITH 1.0μm |||||
| CONDUCTIVE FLUID (ELECTRODE "C") |||||
|  | C | G | B | A |
| C | 519.838144 | -516.80833 | -1.5341793 | -1.4956064 |
| G | -516.66278 | 1877.84656 | -680.6795 | -680.507 |
| B | -1.63541 | -680.50844 | 3299.35881 | -2617.2191 |
| A | -1.4956064 | -680.507 | -2617.2191 | 3299.22 |
| M1 FINGERS "B" SENSED |||||
| CABG | 2617.21906 | pF/cm^2 |  | FLUID GROUNDED |
| ΔC=CABO-CBG | 0.00470668 |  |  | 0.000180% CHANGE |
| CABO | 2617.22377 | pF/cm^2 |  | FLUID FLOATING |
| 1μm/1μm FINGERS y=3.0μm POST HEIGHT, x=5.0μm, z=3.0μm RIDGE HEIGHT |||||
| 5.0μm SENSOR MATERIAL OVER 3.0μm HIGH x 1.0μm WIDE POSTS WITH 1.0μm |||||
| CONDUCTIVE FLUID (ELECTRODE "C") |||||
|  | C | G | B | A |
| C | 458.776625 | -456.00126 | -1.4136874 | -1.3615549 |
| G | -465.97606 | 1783.174 | -658.62144 | -658.57613 |
| B | -1.3000588 | -656.54369 | 3068.26675 | -2438.3123 |
| A | -1.3615549 | -656.57613 | -2438.3123 | 3098.25006 |
| M1 FINGERS "B" SENSED |||||
| CABG | 2438.31231 | pF/cm^2 |  | FLUID GROUNDED |
| ΔC=CABO-CBG | 0.0040638 |  |  | 0.000167% CHANGE |
| CABO | 2434.31638 | pF/cm^2 |  | FLUID FLOATING |
| CHANGE IN CAPACITANCE MATRIX FROM k=3.00 TO k=2.70 SENSOR MATERIAL |||||
|  | C | G | B | A |
| C | 51.0616166 | -50.807075 | -0.1204979 | -0.1340516 |
| G | -50.688225 | 94.6725625 | -22.068062 | -21.930675 |
| B | -0.2364514 | -21.96475 | 201.092063 | -178.90675 |
| A | -0.1340516 | -21.930675 | -178.90475 | 200.971938 |
| % CHANGE IN CAPACITANCE MATRIX FROM 10% CHANGE (k=3.00 TO k=2.70) |||||
|  | C | G | B | A |
| C | 9.823% | 9.831% | 7.854% | 8.963% |
| G | 9.850% | 5.042% | 3.241% | 3.223% |
| B | 14.458% | 3.228% | 6.095% | 6.836% |
| A | 8.963% | 3.223% | 6.834% | 6.091% |

| | | k=3.00 SENSOR MATERIAL | | |
|---|---|---|---|---|
| x 0.5μm M1 FINGERS ON 3.0μm RIDGES (2.5μm SiO2 + 0.5μm SiN) WITH 0.1μm | | | | |
| | INSULATING WATER (Er=80) | | | |
| | | G | B | A |
| | G | 0 | 0 | 0 |
| | B | 0 | 0 | 0 |
| | A | 0 | 0 | 0 |
| | | | | |
| | SHIELD "G" SENSED | | | |
| | CAGG | 680.507 | pF/cm^2 | FLUID GROUNDED |
| | ΔC=CAGO-CAGG | 1.48647072 | | 0.2184% CHANGE |
| | CAGO | 681.993471 | pF/cm^2 | FLUID FLOATING |
| | | k=2.70 SENSOR MATERIAL | | |
| x 0.5μm M1 FINGERS ON 3.0μm RIDGES (2.5μm SiO2 + 0.5μm SiN) WITH 0.1μm | | | | |
| | INSULATING WATER (Er=80) | | | |
| | | G | B | A |
| | G | | | |
| | B | | | |
| | A | | | |
| | | | | |
| | SHIELD "G" SENSED | | | |
| | CAGG | 658.576125 | pF/cm^2 | FLUID GROUNDED |
| | ΔC=CAGO-CAGG | 1.3634224 | | 0.2055% CHANGE |
| | CAGO | 659.929547 | pF/cm^2 | FLUID FLOATING |
| (10% CHANGE) | | | | |
| | M1 FINGERS "B" SENSED | | SHIELD "G" SENSED | |
| | sΔ/CABG | 178.9068 | pF/cm^2 | sΔ/CAGG |
| | sΔ/CABO | 178.907292 | pF/cm^2 | sΔ/CAGO |
| | sΔ/ΔCABG | 44.02669 | "SNR" | sΔ/ΔCAGG |
| | sΔ/ΔCABO | 44.02665 | "SNR" | sΔ/ΔCAGO |
| SENSOR MATERIAL | | | | |
| | | | | |
| | | | | |
| | | | | |
| | | 68.358% | =ELECTROSTATIC SENSING EFFICIENCY (*%Δ | |
| | | | | |

FIG. 13B

FROM FIG. 13B

| 1.0μm SHIELD AND POST TOP WIDTH TAPERING TO 0.6μm | | | | | | |
|---|---|---|---|---|---|---|
| Al2O3 PROTECTION AROUND METAL | | | | | | |
| | | INSULATING GAS (Er=1.00) | | | | |
| | | | | G | B | A |
| | | | G | 0 | 0 | 0 |
| | | | B | 0 | 0 | 0 |
| | | | A | 0 | 0 | 0 |
| | | | | | | |
| | | BOTH "B" AND "G" SENSED | | | | |
| | | CABG-CAGG | 3297.72606 | pF/cm^2 | FLUID GROUNDED | |
| | | ΔC=CAGO-CAGG | 1.4911763 | | 0.0452% | |
| | | CABO-CAGO | 3299.21724 | pF/cm^2 | FLUID FLOATING | |

| 1.0μm SHIELD AND POST TOP WIDTH TAPERING TO 0.6μm | | | | | | |
|---|---|---|---|---|---|---|
| Al2O3 PROTECTION AROUND METAL | | | | | | |
| | | INSULATING GAS (Er=1.00) | | | | |
| | | | | G | B | A |
| | | | G | | | |
| | | | B | | | |
| | | | A | | | |
| | | | | | | |
| | | BOTH "B" AND "G" SENSED | | | | |
| | | CABG-CAGG | 3096.66844 | pF/cm^2 | FLUID GROUNDED | |
| | | ΔC=CAGO-CAGG | 1.357456 | | 0.0438% | |
| | | CABO-CAGO | 3098.24592 | pF/cm^2 | FLUID FLOATING | |

| | | BOTH "B" AND "G" SENSED | | | |
|---|---|---|---|---|---|
| 21.93088 | pF/cm^2 | sΔ/(CABG-CAGG) | 200.837825 | pF/cm^2 | |
| 22.06392 | pF/cm^2 | sΔ/(CABO-CAGO) | 200.971315 | pF/cm^2 | |
| 16.20401 | "SNR" | Δ/Δ/(CABG+CAGG) | 147.948211 | "SNR" | |
| 16.30232 | "SNR" | Δ/Δ/(CABO+CAGO) | 148.046604 | "SNR" | |

| CAB/%Δk) WITH 0.1μm Al2O3 PROTECTION SURROUNDING "A" AND "B" ELECTRODES | | | | | |
|---|---|---|---|---|---|
| | | | | | |

| | | CABG(pF/cm2) | FOR SENSOR AREA OF 0.134 cm2<br>CABG(pF) | MAGNITUDE THIRD ELECTRODE EFFECT<br>ΔC/CABG (%) | RESPONSE (FOR Δk OF -10%)<br>sΔCABG (pF/cm2) | RESPONSE (FOR Δk OF -10% AND SENSOR AREA OF 0.134 cm2)<br>sΔCABG (pF) | RESPONSE (IN %C CHANGE PER %k CHANGE) |
|---|---|---|---|---|---|---|---|
| y=4μm POST HEIGHT, z=3μm RIDGE HEIGHT, x=3μm RF-FLASH 2μm DESIGN, DICK'S 2D SIMULATION | k = 3 | 923.64 | 123.77 | 0.003479% | | | |
| | k = 2.7 | 850.49 | 115.31 | 0.003141% | 63.15 | 8.462 | 0.684 |
| y=4μm POST HEIGHT, z=3μm RIDGE HEIGHT, x=3μm RF-FLASH 2μm DESIGN, DIRK'S 3D SIMULATION | k = 3 | 960.02 | 128.64 | 0.002583% | | | |
| | k = 2.7 | 900.55 | 120.67 | 0.002311% | 59.47 | 7.969 | 0.619 |
| y=3μm POST HEIGHT, z=3μm RIDGE HEIGHT, x=5μm RF-FLASH 1μm DESIGN, DICK'S 2D SIMULATION | k = 3 | 2617.22 | 350.71 | 0.000180% | | | |
| | k = 2.7 | 2438.31 | 326.73 | 0.000167% | 178.91 | 23.974 | 0.684 |
| y=3μm POST HEIGHT, z=3μm RIDGE HEIGHT, x=5μm RF-FLASH 1μm DESIGN, DIRK'S 3D SIMULATION | k = 3 | 2779.88 | 372.50 | 0.000130% | | | |
| | k = 2.7 | 2596.03 | 347.87 | 0.000110% | 183.84 | 24.635 | 0.661 |
| y=4μm POST HEIGHT, z=3μm RIDGE HEIGHT, x=3μm VRF-FLASH 2μm DESIGN, DIRK'S 3D SIMULATION | k = 3 | 2559.06 | 342.91 | 0.002292% | | | |
| | k = 2.7 | 2411.25 | 323.11 | 0.002066% | 147.81 | 19.807 | 0.578 |
| y=3μm POST HEIGHT, z=3μm RIDGE HEIGHT, x=5μm VRF-FLASH=1μm DESIGN, DIRK'S 3D SIMULATION | k = 3 | 8714.06 | 1167.68 | 0.000024% | | | |
| | k = 2.7 | 8101.88 | 1085.65 | 0.000021% | 612.19 | 82.033 | 0.703 |

__US 10,379,074 B2__

SYSTEM AND METHOD FOR SHIELDED CHEMICAL SENSING USING A FINE-LINE SHIELDED SENSING STRUCTURE

TECHNICAL FIELD

This disclosure is generally directed to a system and method for shielded chemical sensing using a fine-line shielded sensing structure.

BACKGROUND

Interdigitated electrode structures for both chemical and non-chemical sensing and transducer applications have been around and described in literature for a long time. They typically include a large number of long and narrow conductors (referred to as "fingers"), arranged in a single plane parallel to one another, and grouped and electrically connected into two- or multiple port electrical elements.

Various nomenclature is used in the technical and scientific literature to identify these types of sensing electrode structures, e.g., IDE (Interdigitated Electrode), FEF (Fringing Electric Field Sensors), Interdigital Sensors and Transducers, and the like. These sensing electrode structures are often implemented as co-planar, patterned metal layers on a substrate, fabricated using thin-film and/or semiconductor type processes. When used as sensors, interdigitated electrodes typically interrogate an area of space between and/or above the metal layers, and detect small changes in the electrical properties of any material or substance occupying that space. A particular concern with such sensors is that the sensors respond only to the electrical properties of the sensor material, and not to the electrical properties of the fluid beyond this sensor material. When a sensor exhibits such an undesired response to the electrical properties of the fluid beyond the sensor material, instead of just to the electrical properties of the sensor material itself, this problem is denoted by terms such as "read-through," commonly used in association with insulating fluids, or the "third electrode effect," commonly used in association with conductive fluids.

SUMMARY

This disclosure provides a system and method for shielded chemical sensing using a fine-line shielded sensing structure.

In a first embodiment, a sensor apparatus includes a substrate, a plurality of parallel interdigitated sensor electrode fingers disposed over the substrate, a peripheral shield disposed over at least some of a periphery of the substrate, and a sensing material disposed in gaps formed by surfaces of the sensor electrode fingers and the peripheral shield.

In a second embodiment, a method for fabricating a sensing structure includes providing a substrate. The method also includes forming a plurality of parallel interdigitated sensor electrode fingers over the substrate. The method further includes forming a peripheral shield over at least some of a periphery of the substrate. In addition, the method includes providing a sensing material in gaps formed by surfaces of the sensor electrode fingers and the peripheral shield.

Other technical features may be readily apparent to one skilled in the art from the following figures, descriptions, and claims.

BRIEF DESCRIPTION OF THE DRAWINGS

For a more complete understanding of this disclosure and its features, reference is now made to the following description, taken in conjunction with the accompanying drawings, in which:

FIG. 3D illustrates 2-D fields capacitance matrix simulation results for both air and water insulating fluid and conducting fluid cases according to this disclosure;

FIG. 3E illustrates a capacitance model obtained from a capacitance matrix for conductive fluid (3-electrode) 2-D fields simulations according to this disclosure;

FIGS. 11A through 13C illustrate capacitance matrices obtained from 2D electrostatic simulations for the FLASh sensor structures of FIGS. 8 and 9A according to this disclosure;

FIG. 16 illustrates field simulation results that compare the VRF-FLASh design of FIG. 15 to the RF-FLASh design of FIG. 14;

DETAILED DESCRIPTION

Figure 1:
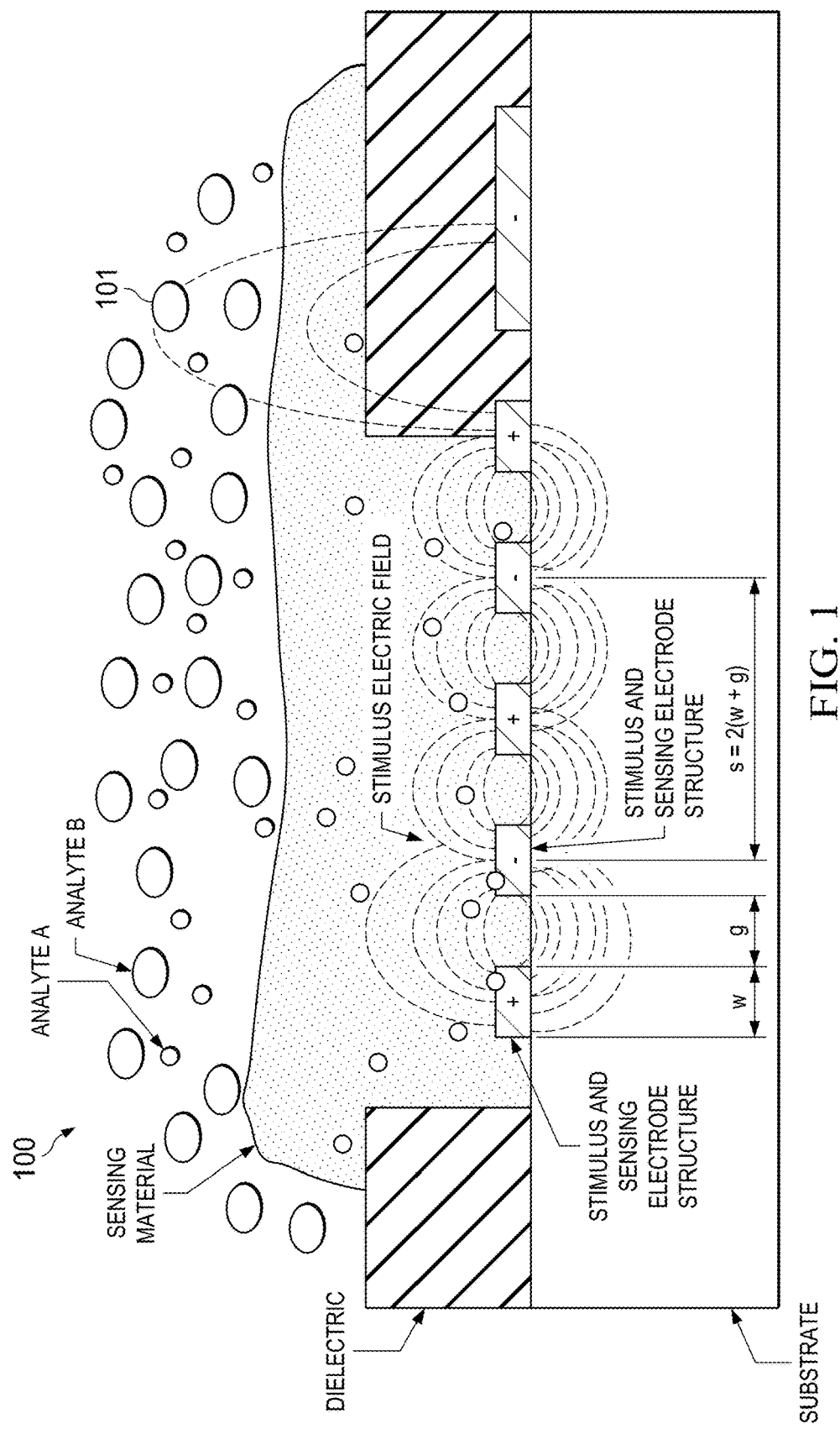
FIG. 1 illustrates an interdigitated sensing structure without a shield that exhibits field protrusion near a discontinuity.

The figures discussed below and the various embodiments used to describe the principles of the present disclosure in this patent document are by way of illustration only and should not be construed in any way to limit the scope of this disclosure. Those skilled in the art will understand that the principles of the present disclosure may be implemented in any type of suitably arranged device or system.

It will be understood that embodiments of this disclosure may include any one, more than one, or all of the features described here. In addition, embodiments of this disclosure may additionally or alternatively include other features not listed here. Although the disclosed embodiments are described with respect to chemical sensing structures, such description is not limiting since the disclosed embodiments are suitable for a wide range of applications.

Embodiments of this disclosure improve the performance (in particular the sensitivity) of chemical sensors, such as those that incorporate an interdigitated electrode structure. These sensors are based on measurements of the relative permittivity (dielectric constant) of thin films of sensor materials which selectively absorb an analyte of interest from the fluid environment and which are deposited on top of the interdigitated sensing electrode structure. The absorption of analyte results in a change in the sensor material's dielectric constant (or other electrical properties), which acts as a representative measure for the concentration of analyte in the fluid in contact with the sensor material's surface. The sensing electrode structure generates a 'stimulus' electric field and detects the changes in dielectric constant (or other electrical properties, such as conductivity) by measuring the resulting electrical current. Preferably, the sensing structure is shielded from any environmental influences such as external electromagnetic fields or external electric charges.

Embodiments of this disclosure provide sensor structures that avoid the undesired "read-through" and "third electrode effect" problems of conventional interdigitated sensors, so that very small changes in the electrical properties of the sensor material (in close proximity to the IDE fingers) can be measured without interference due to changes in the electrical properties of the fluid beyond this sensor material.

In simplified form, an interdigitated electrode structure is considered to form a two-port electrical element, and the electrical impedance between the two ports can be measured. Such measurements can be made by stimulating one port with a sinusoidal or AC voltage ("stimulus voltage") and measuring the AC current ("sense current") drawn out of the second port. An electric field is generated by the stimulus voltage in the space between or near the electrodes, and any changes in the electrical properties of a material occupying that space will have a direct effect on the measured current.

It is known that there is a relationship between the height of the space into which the electrical field lines from co-planar electrode structures protrude, and the lateral dimensions (e.g., width and spacing, or their sum, "pitch") of these electrode structures. The protruding portions of the field beyond the plane of the electrodes are often identified as the "fringing field." A spatial wavelength s can be defined as $s=2*(w+g)$, where w indicates the width of an electrode finger, and g indicates the width of the gap between two electrode fingers. The bulk of the electrical field (e.g., 99% of the energy density), including the fringing field, is contained within one spatial wavelength above or below the plane of the electrode structure.

When creating interdigitated sensors to interrogate selectively absorbing materials, engineers typically select the thickness of these materials on top of the electrode structure to be equal to or more than the spatial wavelength. In the alternative scenario, the sensor will pick up changes in composition of not just the analyte of interest (for instance, a hydrocarbon), but also the physical electrical properties of and connections to the fluid environment right above the sensor material (e.g., the electrical properties of the fluid itself, whether the dielectric constant of an insulating fluid or the conductive and dielectric properties of, and electrical connection to, a conductive fluid), thereby reducing the effective selectivity and sensitivity of the sensor due to this interference.

However, the conductors that electrically connect the ends of the electrode fingers of each port (often referred to as the "bus bars") and any associated connecting lines ("feed lines") to either conductive vias or contact pads (where the signals can be read out) can create discontinuities in the periodic nature of the electric field distribution around the electrode fingers. The discontinuities typically result in the field protruding into open space much further than the amount defined by the spatial wavelength.

For example, FIG. 1 illustrates an interdigitated sensing structure 100 without a shield that exhibits field protrusion near a discontinuity. In the structure 100, the electric field (schematically indicated as curved lines extending between the electrode fingers) is mostly confined within the sensing material and is used to interrogate the presence of analyte A (which selectively diffuses through the sensing material). However, the presence of the discontinuity results in a portion 101 of the electrical field not being confined in the sensing area, and thus also being affected by analyte B, inasmuch as it influences the overall electrical (dielectric or conductive) properties of the fluid itself, and more importantly, anything else that changes the electrical properties of, or in the case of conductive fluids, the electrical connection to, the fluid itself.

Such discontinuities reduce the effective selectivity and sensitivity of the sensor, or require the use of layers of sensing material much thicker than desired in order to avoid this interference. Thick layers grossly reduce sensor response time and tend to create problems in the fabrication and packaging processes for these sensors and are generally undesirable. To mitigate the issue, some existing solutions rely on lateral "shield" or "guard" electrodes, which are co-planar to the sensing electrodes, and are intended to attract the electric field lines away from open space back into the material and/or substrate.

However, these solutions are imperfect, in particular when confronted with structures that are much larger than the spatial wavelength. The desired value of this wavelength can be very small (a few microns), as this allows to integrate a large amount of electrode fingers on a given area, maximizing the response and sensitivity of the sensor; contact pads or vias however are typically much larger, tens or hundreds of microns. This disparity in size results in geometries where good shielding using state-of-the-art lateral co-planar shielding techniques is very difficult or impossible.

In addition to confinement of the stimulus field, to provide adequate selectivity and immunity to noise, an interdigitated sensing structure needs to be protected from the influence of external electric fields or charge distributions. This may be of particular importance in cases where the sensing structure is exposed to electrically conductive fluids (e.g., water with a significant concentration of ions).

Figure 2:
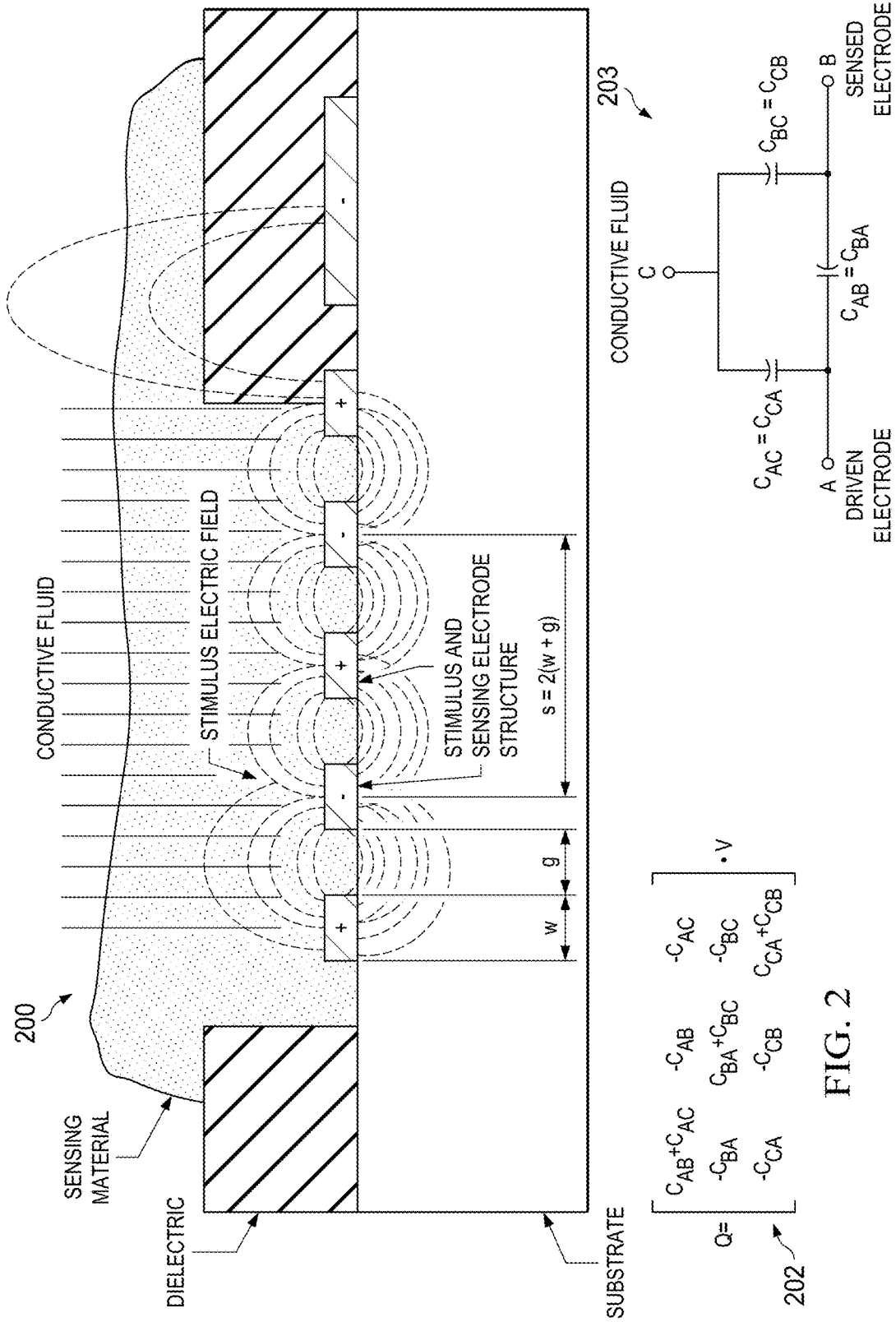
FIG. 2 illustrates an interdigitated sensing structure without a shield that is subject to the "third electrode" effect.

For example, FIG. 2 illustrates an interdigitated sensing structure 200 without a shield that is subject to the "third electrode" effect. As shown in FIG. 2, mobile charges in the fluid can make the fluid conducting, in effect making the conducting fluid itself an electrode on top of the sensor material. As is well understood in electrostatics, the presence of a conductor plane electrode on the opposite side of the insulating sensor material may be viewed as if the dielectric were extended, but embedded with counter (mirror) electrodes carrying the opposite potential of the finger to fluid voltage difference. In this view, the presence of the oppositely-charged mirror electrodes have an effect on the sense current measured at the sense electrode for a given stimulus voltage at the stimulus electrode, and that effect depends on the AC voltage on the fluid electrode itself (For clarity, the analyte(s) are not depicted in FIG. 2, but an aqueous solution containing ions, in concentration sufficient to render the fluid effectively conductive, as one of the fluid phases can be considered). Because the current sensed through the interdigitated finger sensor array varies with the AC voltage on the fluid (and hence the electrical connection to the fluid, this effect acts as a source of interference, sometimes termed "noise" (in the simplified structure depicted in FIG. 2, this effect nominally decays with 1/distance to the surface).

In such a case, the sensing structure 200 cannot be considered a simple two-port element as described before; generally, the electric field can be computed by solving the Poisson equation given a spatial distribution of fixed and/or mobile charges; it can however still be approximated in this situation with a lumped-element model using a Maxwell capacitance matrix 202, if the conductive fluid is assumed to have sufficient conductivity to behave as a conductor (electrode). (The dielectric time constant, Td, which is the product of the resistivity of the fluid [in ohm-cm units] times its dielectric constant [E=Er·Eo, where Er is the relative dielectric constant of the material, and Eo=8.854×10$^{-14}$ F/cm is the permittivity of free space] is the key determinant on whether a fluid is considered to be an insulator or a conductor at a given signal frequency, F. For Td>>½πF, AC currents in the fluid will be dominated by capacitive displacement currents, and the fluid may be considered to be insulating at that frequency. For Td<<½πF, AC currents in the fluid will be dominated by conductive currents, and the fluid may be considered to be conducting at that frequency.) In this case, there are three terminals, interconnected by three capacitive circuit elements, as generally represented by the lumped-element model 203. Solving the capacitance matrix 202 will return the charges (and currents) for a given set of input conditions. It can be seen that the impedance boundary condition on the third terminal (i.e., the conductive fluid, which could be grounded or electrically floating, or potentially at some other AC impedance with respect to ground) will affect the charge or AC current measured on the sense electrode. This is the reason why the undesired interference effect is sometimes referred to as "third electrode" effect.

To provide immunity from this effect, complete electrical shielding of the sensing structure (e.g., by means of a Faraday cage) is sometimes used. Some systems provide a metal shield that is placed in close proximity to an interdigitated sensing structure to attempt to provide immunity to the third electrode effect. However, this approach does not generally provide immunity because the sensor remains sensitive to the electrical properties of the fluid between the shield (which is offset from the surface of the sensor by a gap of finite size) and the sensor surface. For example, if an insulating fluid (such as a gas) is replaced by a conductive fluid (such as water with a reasonably high density of ions present), there will be a measured change in AC current even if no sensed chemical species is present. Hence, while such a spaced grounded Faraday shield should nominally provide a consistent grounded fluid electrode potential to Terminal 3 in FIG. 2, it will not actually prevent the sensed current from reflecting changes in the electrical properties of the fluid (as opposed to the chemical properties it is intended to exclusively sense). Also, in practical applications, an integrated, scalable and miniaturizable approach would be highly preferred.

To address these and other issues, embodiments of this disclosure provide electrical shielding systems for sensing electrodes. The disclosed electrical shielding systems improve the performance and, in particular, the selectivity and noise immunity of chemical sensors, such as those developed by NEOTEK ENERGY, in some embodiments with insulating fluids, and with other embodiments, with either insulating or conductive fluids. These sensors are based on measurements of the relative permittivity (dielectric constant) of thin films of sensor materials which selectively absorb an analyte of interest from the environment and which are deposited over, or on top of, an interdigitated sensing electrode structure. The absorption of analyte results in a change in the sensor material's dielectric constant, which acts as a representative measure for the concentration of analyte in the fluid in contact with the material's surface. The sensing electrode structure generates an electric field and interrogates changes in it to quantify this change. To obtain the best possible selectivity and immunity to external noise sources, the electric field should be confined inside the sensing material, and not protrude elsewhere where it can be affected by the overall electrical properties of the fluid, rather than just the analyte of interest. The sensing structure also should be shielded from any environmental influences such as external electromagnetic fields or external electric charges. The electrical shielding systems disclosed herein provide structures that provide, either for the case of insulating fluids (e.g., peripherally shielded (only) structures), or the general case of insulating or conductive fluids with arbitrary electrical connection (e.g., the peripheral shield plus area shield structures), such confinement of the field and complete shielding of the sensing structure.

The sensing electrodes typically include a metallization pattern on a substrate forming two-port or multi-port electrical elements. In a particular embodiment, the sensing electrodes include a two-terminal interdigitated electrode structure characterized by a spatial wavelength s (as described above). The sensing electrodes are used to interrogate changes in electrical properties of a material deposited above the substrate containing the electrodes (referred to as the "sensing layer"). The pattern of interdigitated lines covered by the sensing layer form the "sensing area," whereas the metallization patterns and lines that electrically tie the interdigitated lines together and route the contacts to pads at the edge of the substrate form the "periphery."

Peripheral Shield

Figure 3A:
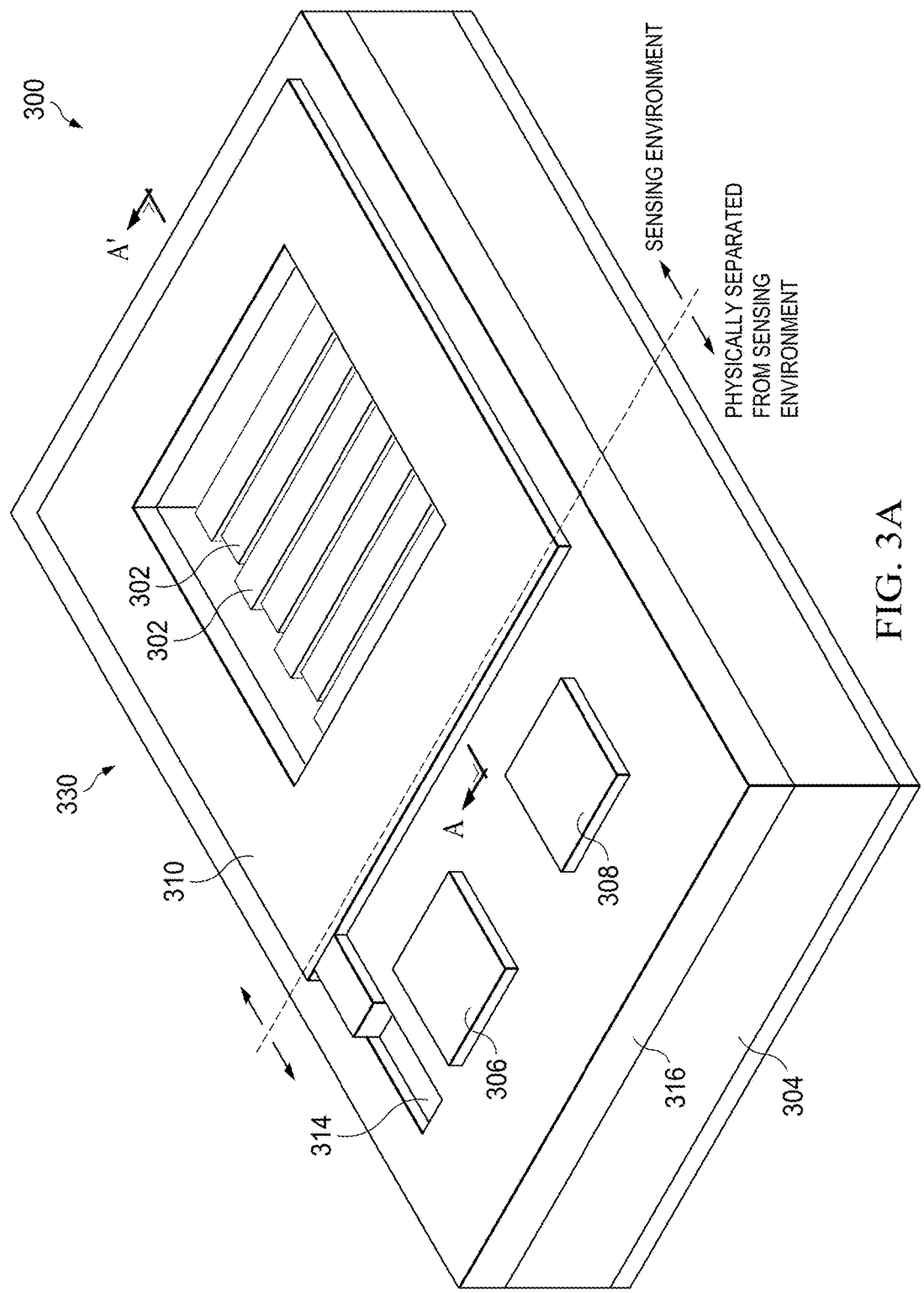
FIGS. 3A and 3B illustrate details of an example peripheral shielded sensor structure according to this disclosure.
Figure 3B:
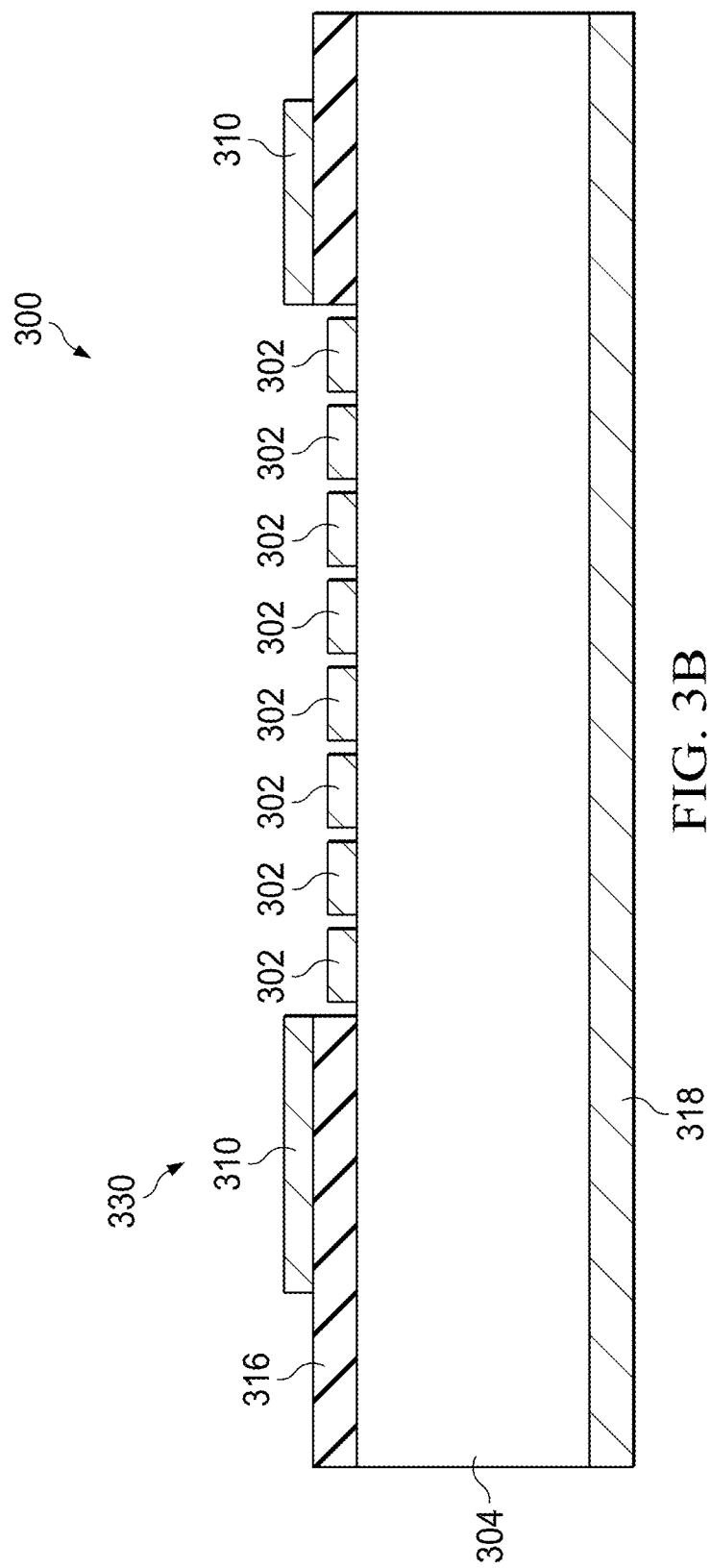

FIGS. 3A and 3B illustrate details of an example electrical shielding system 330 for a sensing electrode structure 300 according to this disclosure. In particular, FIG. 3A shows a top perspective view, while FIG. 3B shows a cross-sectional view taken along the line A-A' in FIG. 3A. Together, the sensing electrode structure 300 and electrical shielding system 330 can be referred to as a peripheral shielded sensor structure. The embodiment of the sensing electrode structure 300 and shielding system 330 shown in FIGS. 3A and 3B is for illustration only. Other embodiments of the sensing electrode structure 300 and shielding system 330 could be used without departing from the scope of this disclosure. Those skilled in the art will recognize that, for simplicity and clarity, some features and components are not explicitly shown in every figure, including those illustrated in connection with other figures. Such features, including those illustrated in other figures, will be understood to be equally applicable to the sensing electrode structure 300 and shielding system 330. It will be understood that all features illustrated in the figures may be employed in any of the embodiments described. Omission of a feature or component from a particular figure is for purposes of simplicity and clarity, and not meant to imply that the feature or component cannot be employed in the embodiments described in connection with that figure.

The sensing electrode structure 300 is an interdigitated sensing structure that includes a plurality of sensing electrode fingers 302 disposed over a substrate 304. The sensing electrode fingers 302 are configured to selectively absorb analyte from the sensing environment and are deposited over the substrate 304 containing the metallization patterns. The sensing electrode fingers 302 are interdigitated as shown in FIG. 3A and have alternating polarities. The substrate 304 can ideally be formed of an insulating material with a smooth surface finish and good mechanical properties, and high resistance to the chemical environments of the fluids of interest, even if it has a relatively high dielectric constant (e.g., single-crystal sapphire). Contact pads 306, 308 for the sensing electrode structure 300 provide a location for soldering or attaching external connections.

The shielding system 330 is disposed above the sensing electrode structure 300 and includes a peripheral shield 310 and a contact pad 314. The shielding system 330 is established by an additional metallization pattern disposed in a plane above the substrate 304 and the sensing electrode fingers 302, and is electrically insulated from the metallization pattern forming the sensing electrode fingers 302 by a (patterned) dielectric layer 316.

The peripheral shield 310 is adjacent to and may slightly overlap the sensing area. The peripheral shield 310 typically covers at least some of the periphery of the substrate 304, i.e., the portions of the substrate 304 which are not part of the sensing area, e.g., the portions containing "bus bars", "feed lines", contact vias, and any other components separate from the periodic nature of the sensing electrodes. It is not necessary to cover with the shield 310 portions of the periphery that are outside of the "sensing environment," that is, the region covered by the fluid.

Figure 4A:
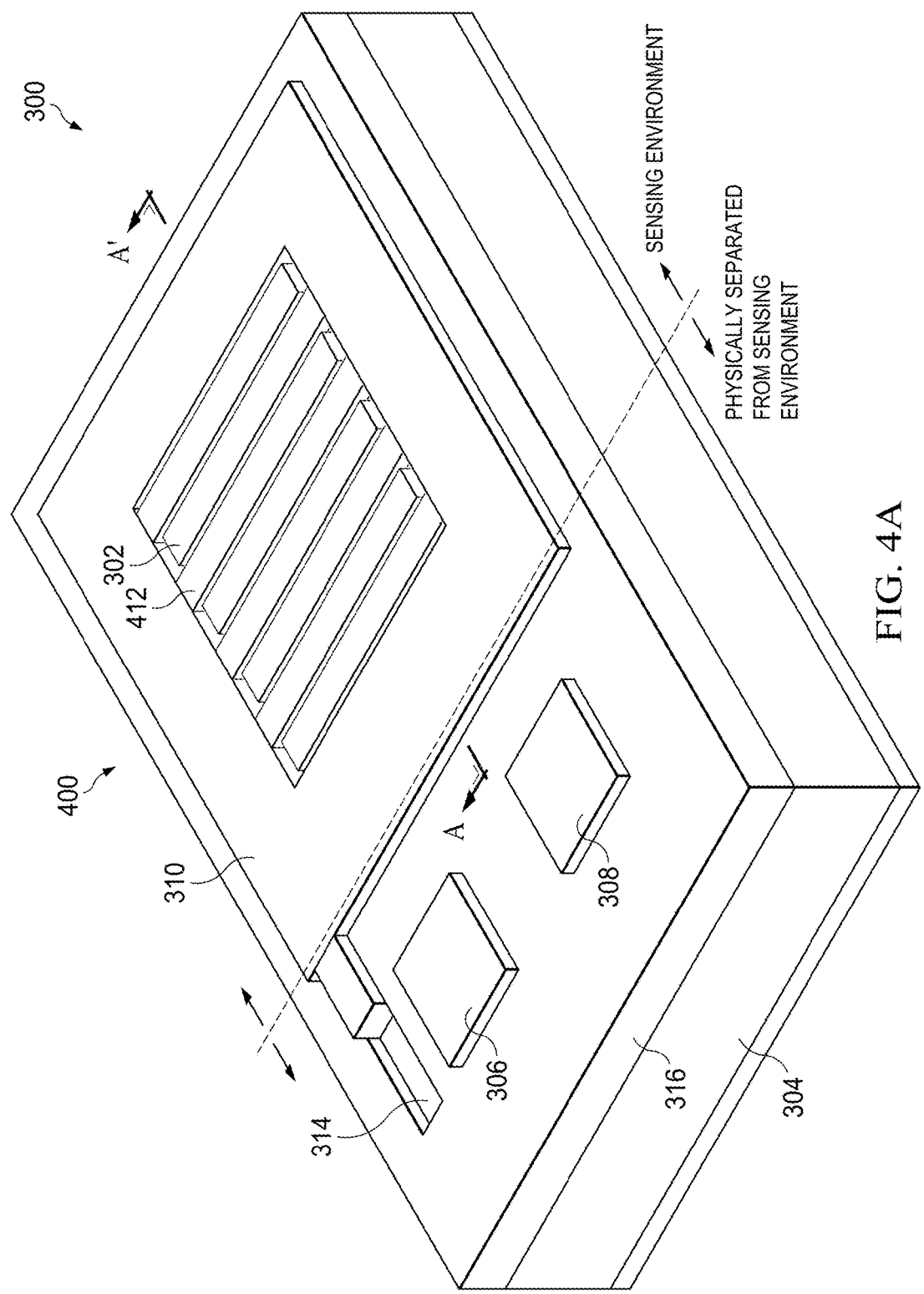
FIGS. 4A, 4B and 4C illustrate details of an example Fine-Line Area-Shielded (FLASh) sensor structure that eliminates the "third electrode effect" issue of the peripheral-shield-only structure to allow the sensor to function with conductive fluids, as well as insulating fluids, according to this disclosure.
Figure 4B:
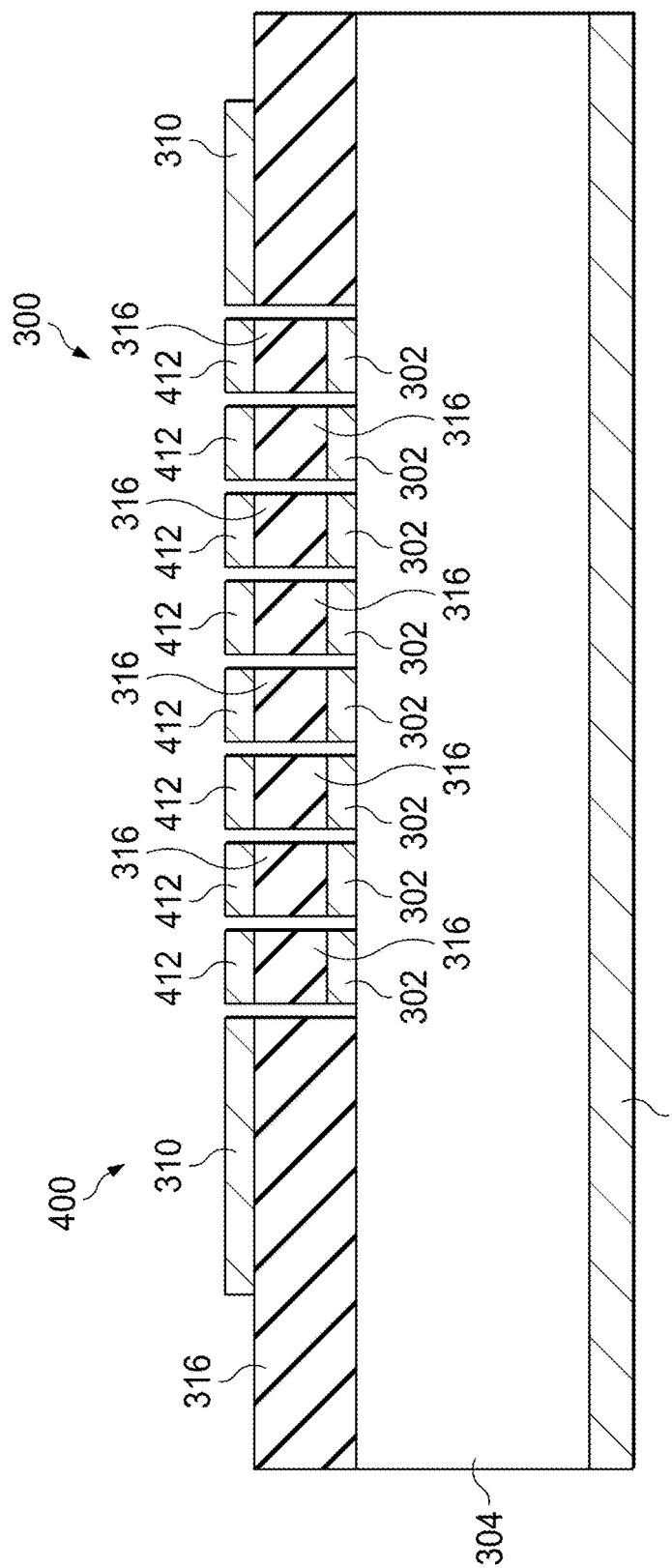
Figure 4C:
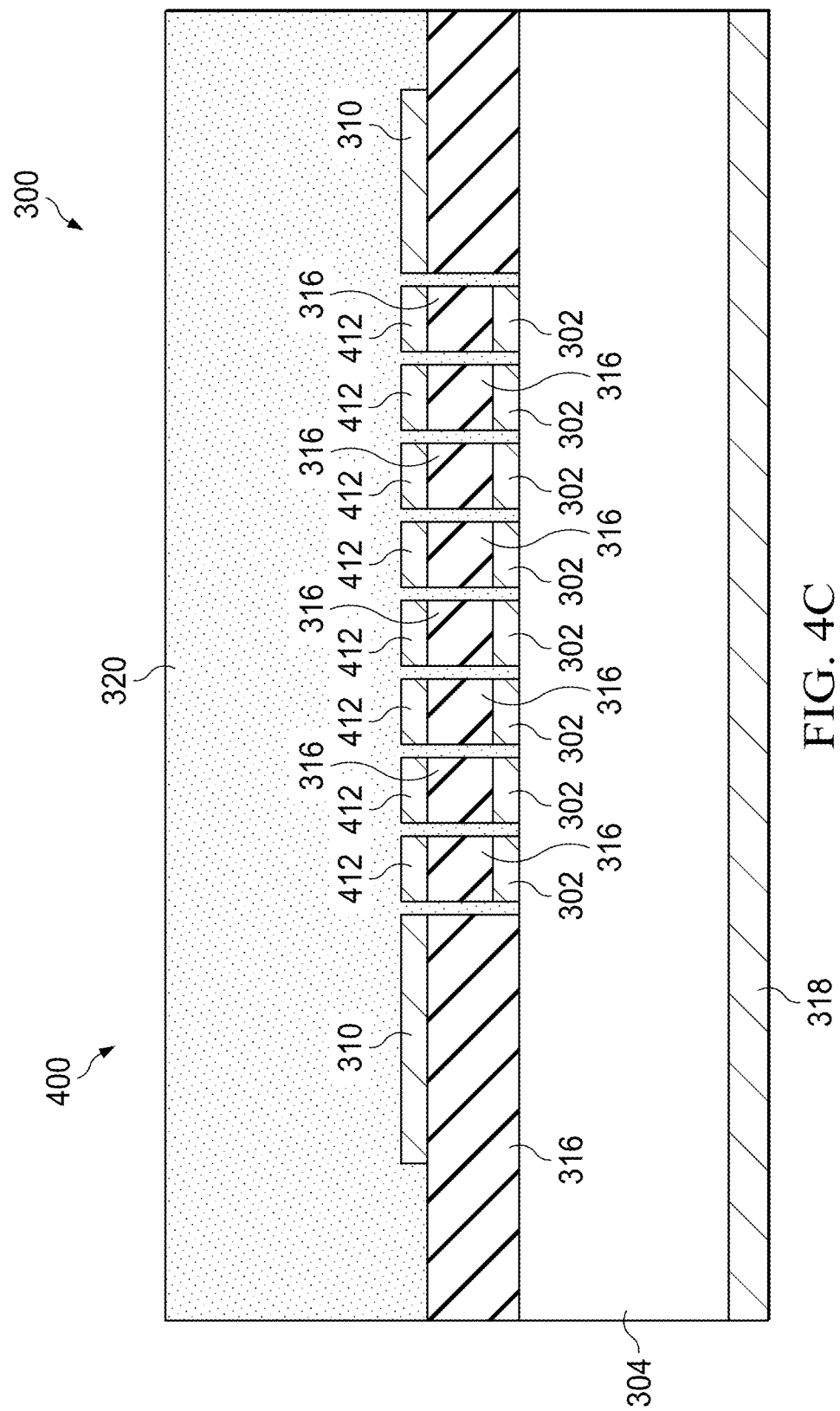
Figure 4D:
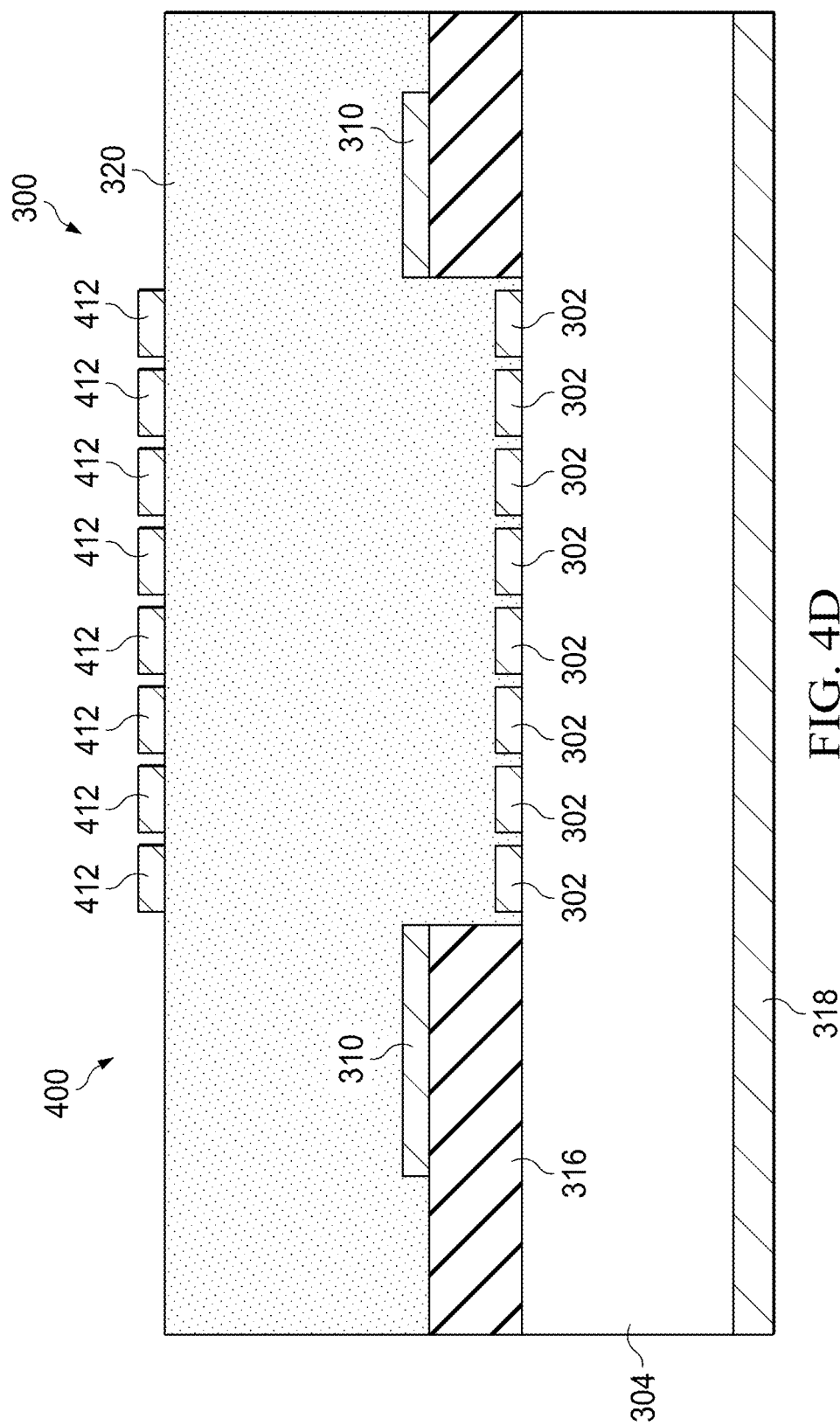
FIG. 4D illustrate details of an alternative embodiment of the FLASh sensor structure according to this disclosure.
Figure 4E:
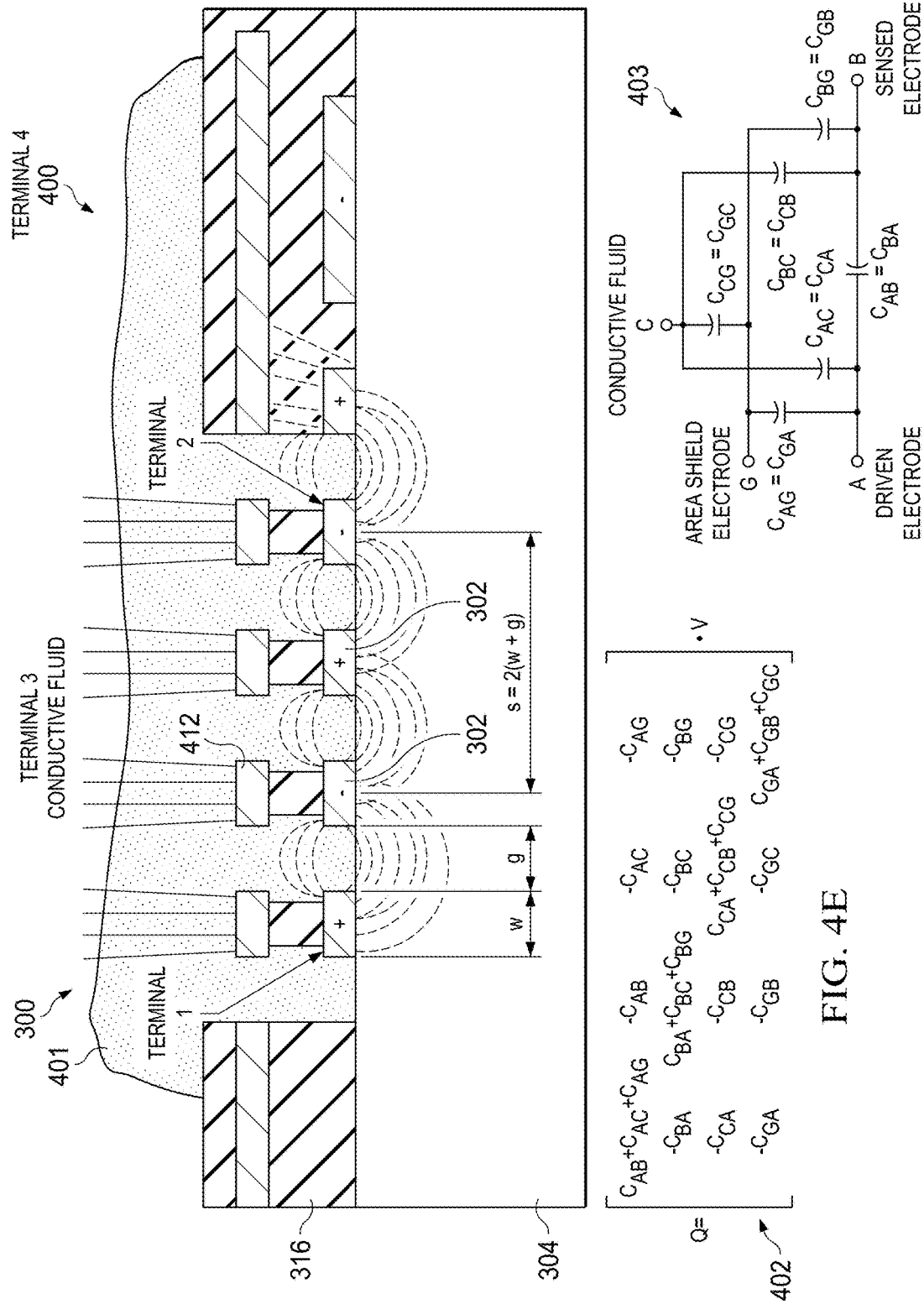
FIG. 4E illustrates additional details of the FLASh sensor structure according to this disclosure.

In working implementations, a sensing material is deposited in between and over the sensing electrode fingers 302 and the peripheral shield 310 (such as shown in FIG. 4E). Only a portion of the overall structure is exposed to the sensing environment containing the analyte or fluid to be analyzed; another portion including the contact pads 306, 308 is physically separated from the sensing environment.

In some embodiments, an additional metallization layer 318 can be formed on the bottom side (and possibly even edges) of the substrate 304 to complete the shielding, as shown in FIG. 3B. (With typical substrate thicknesses, only top and bottom-side shields are necessary, because the field penetration from the sides becomes insignificant beyond a distance of a few substrate thicknesses from the edge of the top and bottom shields.) This is analogous to a closed "Faraday cage" concept. Of course, in many cases this is not required, as the bottom side and edges of the substrate 304 are typically embedded in a grounded metallic housing, which can act as a bottom side shield.

In some embodiments, more than two metallization layers can be incorporated over the top surface of the substrate 304. This allows for more complex geometries and functionality, usually with the top layer used as a shield layer, in a manner similar to the one described above.

In operation, stimulus field lines are formed by the electrical stimulus, such as shown in FIGS. 1 and 2. The peripheral shield 310 prevents the stimulus field lines generated from larger structures like finger contact end electrodes (bus bars) and feed lines, as well as discontinuities, that would otherwise penetrate into the fluid from protruding into the fluid. That is, peripheral shield 310 blocks the portion 101 of the electrical field in FIG. 1 from extending outside of the sensing area. This results in nearly perfect localization or confinement of the electrical field generated by the sensing electrode structure 300 within the sensing material 401, ensuring optimal sensor selectivity and performance.

While the peripheral shield 310 of FIGS. 3A and 3B solve the issue of deep fringing electrical fields from the end electrodes for non-conductive fluids (such as depicted at 101 in FIG. 1), the peripheral shield 310 is not a complete solution for conductive fluids. In some implementations where conductive fluids are used, additional shielding is beneficial, as discussed below.

It is well known that electrostatic fields from interdigitated sensor fingers, aside from contact electrode effects, die off exponentially as the thickness of the insulating sensor material is increased. 2-D fields simulations with insulating fluids such as gas (k=1.00), pure oil (k=2.00) and pure water (k=80) show the expected exponential decrease in the differences in the sensor capacitance between these different dielectric fluids, as the sensor layer thickness is increased.

A difference between an insulator (even a high dielectric constant insulator) and a conductor is that the conductor can terminate electrostatic flux lines in a way an insulator cannot. This difference has implications for area-unshielded, perimeter-shielded sensor geometry in the presence of a conducting fluid. When a grounded conducting fluid is placed on the surface of the sensor material, the result is the same as if image electrodes with the opposite voltage applied were created equidistant on the opposite side of the conductor plane. This has the result that the capacitive flux from the +V on the driven "A" fingers to the sensed "B" fingers is partially cancelled by the −V on the mirrored image "A" fingers, so this $C_{ABG}$ sensor capacitance with grounded conducting fluid is substantially lower than with an insulating fluid.

The persistence of the presence of the changes in sensor impedance upon immersion in fluids implies either that there is an electrostatic phenomenon or a physical phenomenon. These sensor behavior observations can be understood by more detailed interpretation of the 2-D electrostatic simulation results.

In many cases, chemical sensors operate in one of three environments: gas (insulating), conductive liquid (e.g., brine), or non-conductive liquid (e.g., insulating oil or pure water). For the conductive fluid case, an electrical connection to the fluid independent from the sensor may also be present (e.g., the fluid might be grounded).

It can be observed that in a pure liquid environment, some sensors exhibit "memory" effects, presumably due to an interface film buildup on the surface of the sensor material. One way to address this issue is to operate the sensors in a "power washer" mode, in which the liquid is entrained as droplets in a high gas velocity spray, where the droplet kinetic energy upon impingement on the sensor surface is sufficient to blast off any surface film and prevent buildup to allow proper analysis of the incoming fluid stream, devoid of history effects. Providing a tightly-controlled liquid-gas ratio (LGR) in an optimized gas velocity stream should achieve the desired sensor operation. Also, by simply periodically setting the liquid flow rate to zero (LGR=0), sensor baseline drift can be addressed. The use of high velocity gas-only (LGR=0) operation to measure the baseline sensor capacitances (impedances) can be helpful in overcoming the long-term baseline drift problems that could otherwise limit the effective sensitivity of chemical sensors.

The sensors are to be baselined in an insulating gas environment, and then used for measurement of fluid in an impinging droplet form in which any electrical connection of the droplets to ground will presumably be uncertain. For properly baselined, low dynamic noise operation, the sensor electrostatics would have to be robust (meaning effectively zero shift in measured sensor differential capacitance between gas, isolated conductive liquid and grounded conductive liquid operation). Some sensor electrode geometries cannot provide that capability. The 2-D fields simulation explains this.

The 2-D fields simulation produces a capacitance matrix for a configuration of two to four electrodes with up to four different dielectric constant insulating regions. In the simulations, "A" and "B" are chosen for the sensor finger electrodes (the only electrodes in the insulating fluid case, aside from the peripheral shield, which lies outside of the interdigitated finger array portion of the sensor), plus "C" for the fluid electrode in the perfectly conducting fluid case. For the dielectrics, "R" is used for the sapphire substrate (Er=9.80), "N" for SiN (silicon nitride, Er=6.00), "0" for insulating water (Er=80) and "P" for air (gas) (Er=1.00). The simulation covered two "A" and two "B" fingers and the four gaps in between for a 16 μm width. The simulation started and ended at the center of "B" fingers and used insulating boundaries so that, by reflection, the fields are the same as if the array were infinite in extent (but the capacitance matrix values are only for the 16 μm wide by 1 cm finger length area, or 0.0016 $cm^2$ area, and hence to convert simulation C values (in pF) to C/A values (in pF/$cm^2$) they must be divided by 0.0016 $cm^2$).

To understand the 2-D fields simulation results, it is helpful to understand a capacitance matrix. The AC current, I, through a capacitor with an AC voltage V at frequency f applied across it is $I=j(2\pi f)VC$. (For purposes of understanding the sign conventions and meaning of the matrix, it may be more convenient to think of a conductance matrix where I=GV, where these can be simple DC voltages and currents.) In this characterization, all of the ports are assumed to be operating at a zero impedance (e.g., zero source impedance and zero ammeter impedance). In a 2-electrode simulation (i.e., a sensor with an insulating fluid with just "A" and "B" electrodes), the capacitance matrix consists of only four entries, $C_{AA}$, $C_{AB}$, $C_{BA}$, $C_{BB}$, and the magnitude of these four capacitance matrix terms is identical. The signs of $C_{AA}$ and $C_{BB}$ are positive, while the signs of $C_{AB}$ and $C_{BA}$ are negative, because the current direction is opposite when the voltage source is placed on the "B" electrode while the ammeter is located on the "A" electrode, instead of the ammeter and voltage source being connected in series on the "A" port, with the "B" port grounded.

Some 2-D simulation results have been conducted for this insulating fluid case. The rationale behind that is that the water dielectric constant (Er=80) is so high in comparison to normal materials like air (k=1.00) or sensor material (k=3.00) that the voltage drops for a given flux density would be very small, and practically conductor-like in nature. Also, these simulations show the expected exponential drop-off of $\Delta C_{AB}(x)$ with x, where $\Delta C_{AB}(x)$ is the change in $C_{AB}$ from air to water [$\Delta C_{AB}(x)=C_{AB}(\text{water})-C_{AB}(\text{air})$ for sensor material thickness x over the top of the sensor fingers], which shows an x=4 μm to 6 μm sensor layer thickness should be adequate for very low electrostatic feedthrough.

FIG. 3C illustrates results from simulations of electrostatic feedthrough ("read-through") for insulating fluids using two-electrode 2-D fields simulations of a peripheral-shield-only structure according to this disclosure. The solid line illustrates the results (the change in sensed capacitance observed when the fluid is changed from insulating air to insulating (high-purity) water), showing the exponential decrease of this change in capacitance as the thickness of the sensor material is increased. Since only a 5.3 micron thickness of sensor material is sufficient to suppress this read-through error to 0.01%, this peripheral-shield-only structure is quite satisfactory for use with insulating fluids. However, these results do not carry over to the conducting fluid case where the "third electrode effect" produces sensor output changes due to changes in the electrical connection to the conductive fluid.

Practically, the treatment of (ordinary, as opposed to ultra-pure) water as an insulator is not realistic. A better insulator would exhibit very small conductive currents in comparison to the capacitive displacement currents at the frequency of interest (1% or less would be good). Typically, in small (e.g., drop-sized) distilled water samples, the conductance levels are too high, so the use of conducting fluids in testing is more practical.

While the fact that hyper-pure "suitably insulating" water (for purposes of measurements at signal frequencies of the order of 70 KHz) is seldom encountered, and easily ionic-contaminated to a more conductive state, there is conceptual reason to suspect treating, for electrostatic analysis purposes, a very high dielectric constant insulator as being "a lot like a conductor", which would tend to make the two-electrode insulating fluid analysis acceptable. There is a conceptual difference between an insulator with a very high dielectric constant, which can pass a high flux density at a low potential drop, and a conductor, which can do that and also terminate flux. That is an important conceptual difference, which can have a major impact on the electrostatic fields simulation results.

The 3-electrode 2-D fields simulation results can be illustrated by showing the actual capacitance matrix results for the case of a conducting electrode "C" on top of the sensor material that lies over the interdigitated "A" and "B" sensor electrodes, the three-electrode 9-element matrix, along with the two electrode 4-element matrices for the air and insulating water cases. These capacitance matrices are shown in FIG. 3D (after conversion to C/A values for the case of k=6.0 SiN with thicknesses of x=5 μm (upper row of results) and x=2 μm (lower row). (Nominal sensor area=0.13297 cm$^2$.)

FIG. 3D illustrates 2-D fields capacitance matrix simulation results for x=5.0 μm and x=2.0 μm thicknesses of SiN over the top of 2 μm lines/spaces sensor fingers for both the air and water insulating fluid and conducting fluid cases. Note that $C_{ABG}$ and $C_{ABO}$ rows below the capacitance matrices are the results of calculation based on interpretation of the capacitance matrix results, representing the measured sensor capacitance under different fluid grounding conditions, using the model of FIG. 3E.

Figure 3C:
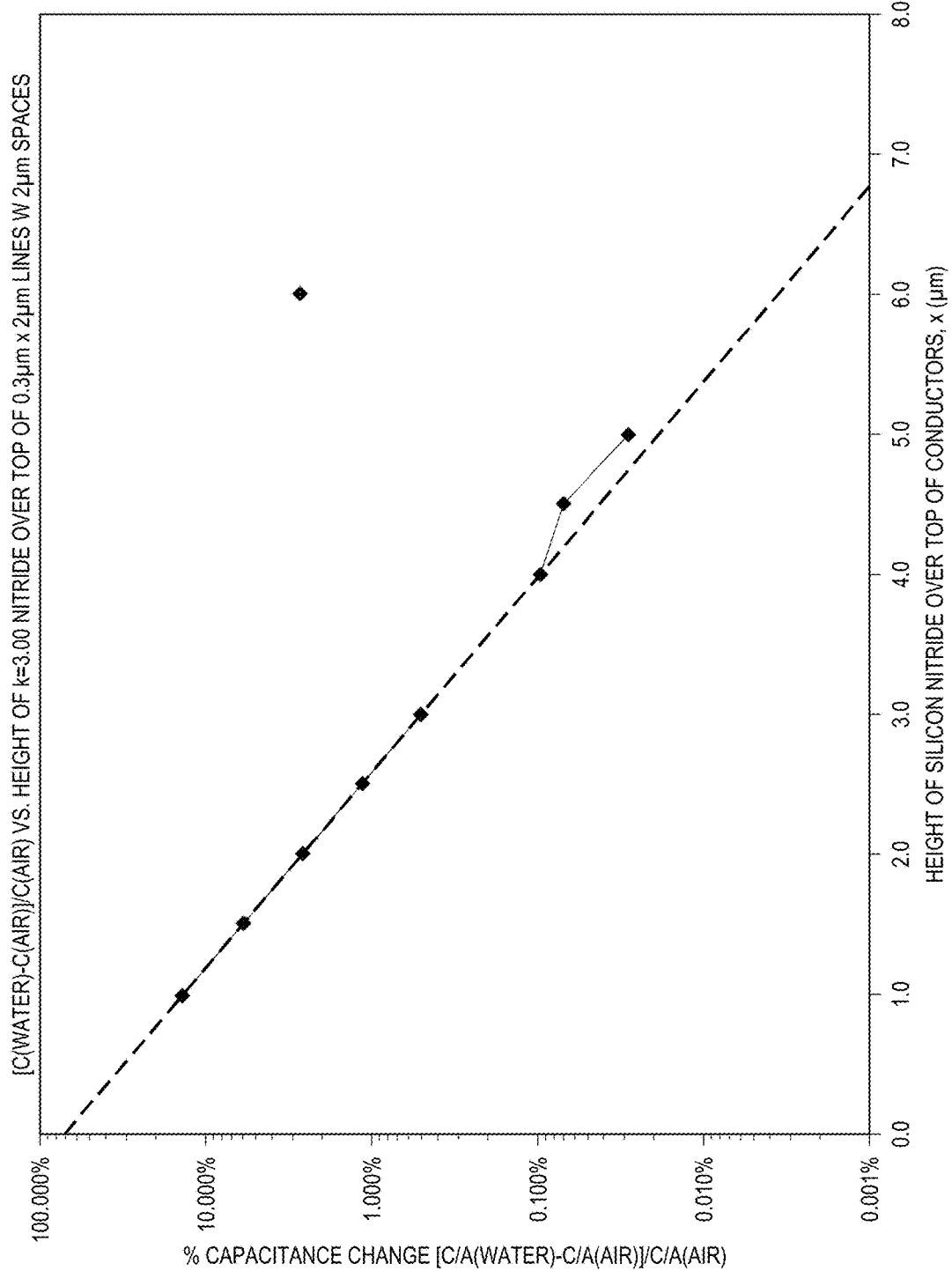
FIG. 3C illustrates results from simulations of electrostatic feedthrough for insulating fluids using two-electrode 2-D fields simulations according to this disclosure.

As would be predicted from FIG. 3C, for the thicker, x=5.0 μm dielectric, there is only a tiny increase in the sensor $C_{AB}$ when the sensor is moved from air to insulating water (upper row center and right 2×2 C/A matrices), whereas for the thinner (field penetrating) x=2.0 micron dielectric, there is a significant (about ΔC/A=80 pF/cm$^2$) increase from air to insulating water (lower row center and right 2×2 C/A matrices). The 3×3 capacitance matrix is obtained from two different 2-D electrostatic fields simulations (e.g., with electrodes "B" and "C" grounded and "A" driven for one, and with "A" and "B" grounded and "C" driven for the other simulation).

FIG. 3E illustrates a capacitance model obtained from the capacitance matrix for the conductive fluid (3-electrode) 2-D fields simulations according to this disclosure. Note that while the capacitance matrix is defined for zero AC impedance on all electrodes, this circuit model of the sensor is applicable for any arbitrary impedances on the three ports. In normal operation, the "A" and "B" sensor finger electrode ports are operated at nominally zero impedance, and the conductive fluid "C" electrode might be shorted to ground, floating, or with some other impedance to ground such as the capacitance of a long ground wire (possibly with someone holding it), or an overlapping brine drop experiment in which there is a capacitance to a grounded peripheral shield. In all such cases, the measured response is calculated as a circuit problem given the various applied port impedances or capacitances.

Because there are finite computational errors in the simulations, small, but noticeable, variations may be apparent between matrix values. It is easier to visualize the meaning of the capacitance matrix entries by looking at the capacitance model generated from the capacitance matrix, as shown in FIG. 3E.

The capacitance model of FIG. 3E contains only the off-diagonal elements of the capacitance matrix; the diagonal elements are obviously $C_{AA}=C_{AB}+C_{AC}$, $C_{BB}=C_{BA}+C_{BC}$ and $C_{CC}=C_{CA}+C_{CB}$, so all of the capacitance matrix information is captured in this model. The 2-D fields simulations give all of these capacitance matrix values directly for the simulated area (240 μm×1 cm for these simulations). Looking from right to left in the top row of matrices in FIG. 3D, it shows for air $C_{AB}$=1977.6539 pF/cm$^2$, for insulating water $C_{AB}$=1978.2722 pF/cm$^2$ (only slightly larger, as expected), but in the 3×3 matrix the $C_{AB}=C_{BA}$=1721.5274 pF/cm$^2$ values are much smaller. The reason for that is that because of the definition of the capacitance matrix (in which all ports are grounded), this $C_{AB}=C_{BA}$=1721.5274 pF/cm$^2$ value corresponds to the case when the fluid is shorted to ground, $C_{ABG}$. For the $C_{ABO}$ floating conductive fluid case (which is expected to be close to the insulating fluid $C_{AB}$ results), the circuit calculation for $C_{ABO}$ is performed. With the conductive fluid completely floating (as in a brine drop experiment with no shield overlap and no ground wire touching the drop), the combined capacitance measured from "A" to "B", $C_{ABO}$, will be the parallel combination of $C_{AB}$ in parallel with the series combination of $C_{AC}$ and $C_{BC}$. That is, $$C_{ABO}=C_{AB}+(1/C_{AC})+(1/C_{BC}) \qquad \text{Equation 1}$$

where $C_{ABO}$ is the measured capacitance with conductive fluid floating, and $C_{AB}$, $C_{AC}$, and $C_{BC}$ are the values from the capacitance matrix.

The calculated $C_{ABO}$ value is shown under the 3×3 matrices in FIG. 3D, and for x=5.0 μm SiN, using $C_{AC}$=514.007 pF/cm$^2$ and $C_{BC}$=513.9 pF/cm$^2$, the calculated value is $C_{ABO}$=1978.501 pF/cm$^2$, just slightly higher than the insulating water $C_{AB}$=1978.2722 pF/cm$^2$ result.

As expected for a thinner x=2.0 μm case (bottom row of capacitance matrices in FIG. 3D) with substantial field penetration beyond the dielectric surface into the fluid, for air $C_{AB}$=1940.1253 pF/cm$^2$, substantially increasing with insulating water to $C_{AB}$=2020.6648 pF/cm$^2$, and slightly further increasing with floating conducting brine to $C_{ABO}$=2034.6232 pF/cm$^2$, but when the brine is grounded, there is a large drop to only $C_{ABG}$=1422.4549 pF/cm$^2$ due to the strong shielding effect of the grounded fluid only 2 μm above the sensor fingers.

It was calculated (using best-fit circle technique) that the drop covered 31.476% of the 0.13297 cm$^2$ sensor area, meaning the drop-covered area was 0.04185 cm$^2$ and the air-covered area was 0.09116 cm$^2$. Using the air $C_{AB}$=1940.1253 pF/cm$^2$ value, the initial (before drop) capacitance should have been 257.98 pF and the air-covered portion after the brine drop was put down should have a capacitance of 176.87 pF. With the brine drop floating, $C_{ABO}$=2034.6232 pF/cm$^2$, the capacitance under the drop should be 85.157 pF, for a total sensor capacitance of 262.024 pF, a 1.57% increase in calculated capacitance over the no-drop (all air) initial case. When the drop is grounded by inserting the ground wire into the drop, the calculated C/A from FIG. 3D is $C_{ABG}$=1422.4549 pF/cm$^2$, for a capacitance of 58.535 pF under the drop, or a total sensor capacitance of 236.40 pF, which is a drop of −8.36% relative to the initial air case, or −9.78% relative to the floating drop case. Experimental data had Z=8129 ohms with all air, 8041 ohms with the brine +3.46% in Zdrop floating (−1.08% in Z, or +1.08% in C), and 8319 ohms with the drop grounded (+3.46% in Z or −3.46% in C relative to the floating drop case). The absolute magnitude of C (air-only) of $C_{AB}$=257.98 pF would give an impedance at f=69,300 Hz of −j8902 ohms, in reasonable agreement with the measured 8129 ohms (and if the conductor thickness had been increased to 0.45 μm in the 2-D simulations, this would increase the capacitance/reduce impedance, giving closer agreement).

Thus, it can be seen that, even with "thick enough" (x>5 μm) sensor layer thicknesses, there will be very substantial shifts in sensor capacitance between the air or insulating fluid case and the grounded conducting fluid case (e.g. from $C_{ABO}$=1978.501 pF/cm$^2$ to $C_{ABG}$=1721.5274 pF/cm$^2$ for the x=5.0 μm k=6.0 SiN case of FIG. 3D, a −13% change). In the case of k=3 sensor material, the capacitance shift at any given thickness, x, is smaller (because the effective thickness is the physical thickness divided by the square root of the dielectric constant, k). In relation to the image charge view of how the presence of a grounded conducting fluid on the sensor material surface acts to reduce $C_{AB}$, the magnitude of the shift should nominally vary as 1/x.

Figure 3F:
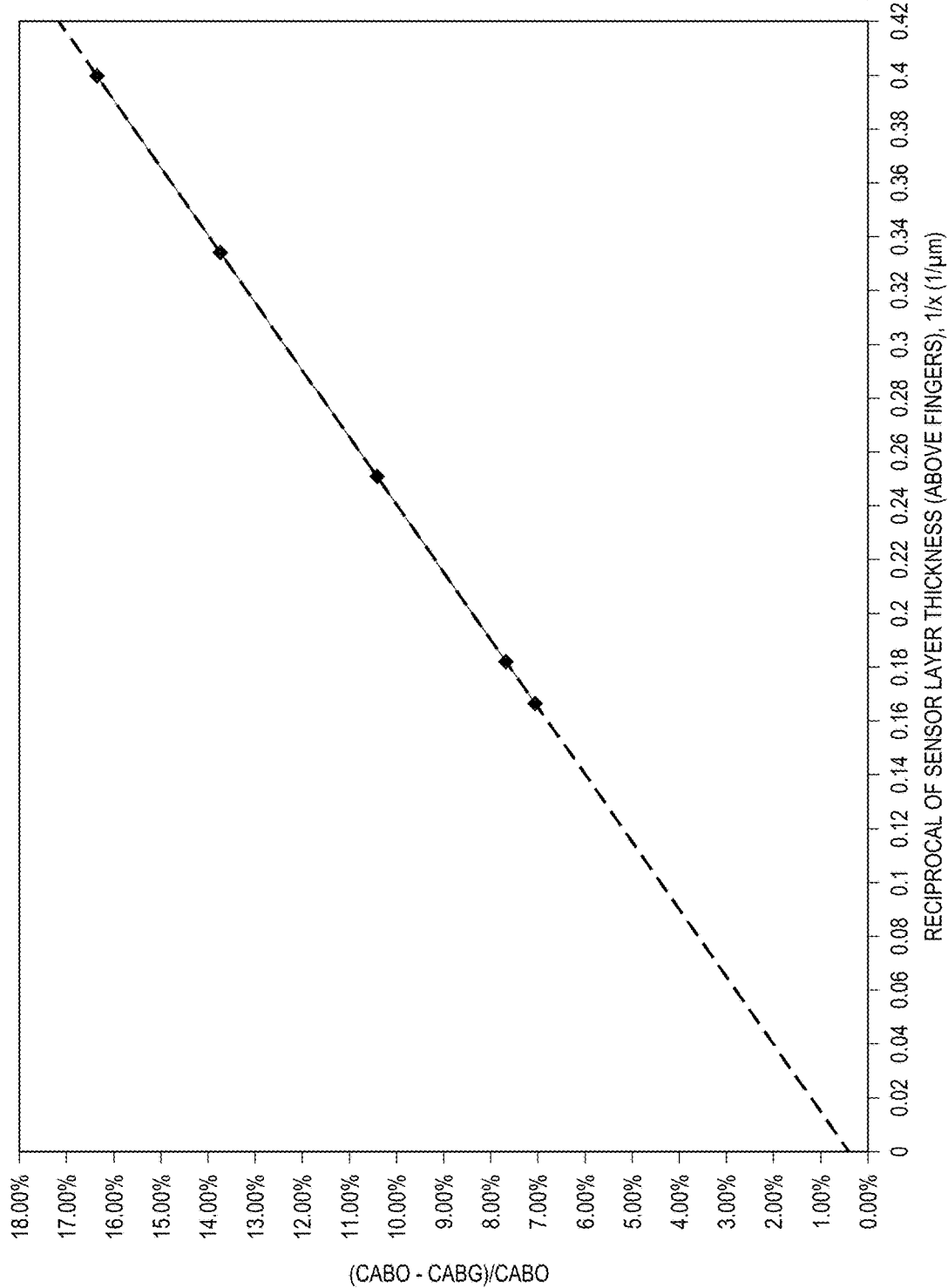
FIG. 3F illustrates 2-D fields simulation data points of capacitance shift between floating and grounded conductive fluid (the "third electrode effect") of a peripheral-shield-only structure according to this disclosure.

FIG. 3F illustrates 2-D fields simulation data points (solid heavy line) of capacitance shift between floating and grounded conductive fluid, $(C_{ABO}-C_{ABG})/C_{ABO}$, plotted versus reciprocal of the thickness of the k=3.0 sensor material (above the 2 µm lines and spaces, 0.3 µm thick sensor fingers), 1/x. The dashed line is an extrapolation from the X=2.5 µm to x=6.0 µm simulation region to larger thicknesses (smaller 1/x). Note that while this extrapolation line suggests a small offset at 1/x=0, presumably the real curve would go to 0.00% at 1/x=0. In any event, even at super-large, x>50 µm, thicknesses (=fragile layers with very slow response), the ~1% ΔC shifts are too large.

What is clear from FIG. 3F is that because of the slow, 1/x, reduction of the $(C_{ABO}-C_{ABG})/C_{ABO}$ capacitance shift between floating and grounded conductive fluid with sensor layer thickness for some peripheral-shielded interdigitated sensor array structures, it would not be possible to achieve 0.1% ΔC levels, even with large (X>50 µm) sensor layer thicknesses. With any reasonable sensor layer thicknesses (e.g., x=10 µm or less), the capacitance shift going from the floating or insulating fluid to a grounded fluid is too large to work with adequate sensitivity in a "power washer" spray mode. In such circumstance, an area-shielded sensor substrate design may be advantageous, as described below.

FLASh

FIGS. 4A, 4B and 4C illustrate details of another example electrical shielding system 400 for the sensing electrode structure 300 according to this disclosure. In particular, FIG. 4A shows a top perspective view, FIG. 4B shows a cross-sectional view taken along the line A-A' in FIG. 4A, and FIG. 4C shows a cross-sectional view with a sensing material added to the structure. Together, the sensing electrode structure 300 and electrical shielding system 400 can be referred to as a Fine-Line Area-Shielded (FLASh) sensor structure. The embodiment of the sensing electrode structure 300 and shielding system 400 shown in FIGS. 4A through 4C is for illustration only. Other embodiments of the sensing electrode structure 300 and shielding system 400 could be used without departing from the scope of this disclosure.

As in FIGS. 3A and 3B, the sensing electrode structure 300 of FIGS. 4A-4C is an interdigitated sensing structure that includes a plurality of sensing electrode fingers 302 disposed over a substrate 304. Contact pads 306, 308 for the sensing electrode structure 300 provide a location for soldering or attaching external connections.

The shielding system 400 is disposed above the sensing electrode structure 300 and includes a peripheral shield 310, an area shield 412, and a contact pad 314. The shielding system 400 is established by an additional metallization pattern disposed in a plane above the substrate 304 and the sensing electrode fingers 302, and is electrically insulated from the metallization pattern forming the sensing electrode fingers 302 by a (patterned) dielectric layer 316.

The peripheral shield 310 is adjacent to and may slightly overlap the sensing area. The peripheral shield 310 typically covers at least some of the periphery of the substrate 304, i.e., the portions of the substrate 304 which are not part of the sensing area, e.g., the portions containing "bus bars", "feed lines", contact vias, and any other components separate from the periodic nature of the sensing electrodes.

The area shield 412 is disposed vertically above the sensing electrode fingers 302, and includes a pattern of lines collinear to the sensing electrode fingers 302; however, unlike the latter, the area shield 412 is not an interdigitated two-terminal element. Instead, the lines that form the area shield 412 are physically and electrically connected together, and tied to the same reference potential as the peripheral shield 310. This potential can be (but may not be) the same as the reference potential, i.e. ground, of the measurement system; as long as the potential is constant, the shielding system 400 will function as desired).

In working implementations, a sensing material 320 is deposited in between and over the vertical features formed by the sensing electrode fingers 302 and the area shield 412 (as shown in FIG. 4C). Only a portion of the overall structure is exposed to the sensing environment containing the analyte or fluid to be analyzed; another portion including the contact pads 306, 308 is physically separated from the sensing environment.

In some embodiments, an additional metallization layer 318 can be formed on the bottom side (and possibly even edges) of the substrate 304 to complete the shielding, as shown in FIGS. 4B and 4C. (With typical substrate thicknesses, only top and bottom-side shields are necessary, because the field penetration from the sides becomes insignificant beyond a distance of a few substrate thicknesses from the edge of the top and bottom shields.) This is analogous to a closed "Faraday cage" concept. Of course, in many cases this is not required, as the bottom side and edges of the substrate 304 are typically embedded in a grounded metallic housing, which can act as a bottom side shield.

In some embodiments, more than two metallization layers can be incorporated over the top surface of the substrate 304. This allows for more complex geometries and functionality, usually with the top layer used as a shield layer, in a manner similar to the one described above.

FIG. 4D illustrates details of an alternative embodiment of the electrical shielding system 400 for the sensing electrode structure 300 according to this disclosure.

As shown in FIG. 4D, the electrical shielding system includes the peripheral shield 310 and an area shield 412. However, in this embodiment, the area shield 412 is disposed over the sensing material 320 instead of the sensing material 320 being disposed over the area shield 412.

FIG. 4E illustrates additional details of the sensing electrode structure 300 and electrical shielding system 400 according to this disclosure. As shown in FIG. 4E, the sensing electrode fingers 302 have alternating polarities. Each finger 302 has a width w and is separated from the adjacent finger 302 by a gap of width g. A sensing material 401 is deposited in between and over the vertical features formed by the sensing electrode fingers 302 and the area shield 412.

The structure 300 and shielding system 400 can be modeled as a four-terminal model, interconnected by capacitive circuit elements, and can be generally represented by the lumped-element model 403. Here, the fourth terminal is the shielding system 400. The efficacy of the area shield 412 can be calculated using the capacitance matrix 402. The capacitance values in the matrix 402 are determined by the geometry and materials of the shielding system 400, and can be calculated using, e.g., finite element field simulations. The main parameters determining the efficacy of the area shield 412 are the gap g between the shield lines and the height of the dielectric posts formed by the dielectric layer 316 between the sensing electrode fingers 302 and the corresponding shield lines.

In operation, stimulus field lines are formed by the electrical stimulus. The stimulus field lines are shown as curved lines, whereas the field lines as a result of the mobile fluid charge (indicated as circles with plus signs and identified as "Terminal 3") are shown as lines that extend between the area shield 412 and the circles. In the shielded structure 300, the latter terminate on the area shield 412 and generally do not affect the sensing structure and sense current, making the device immune to the effects of the external charge. The peripheral shield 310 prevents the stimulus field lines from protruding into the fluid (compare FIG. 4E to the field lines shown in FIG. 2). This results in nearly perfect localization or confinement of the electrical field generated by the sensing electrode structure 300 within the sensing material 401, ensuring optimal sensor selectivity and performance.

Figure 5:
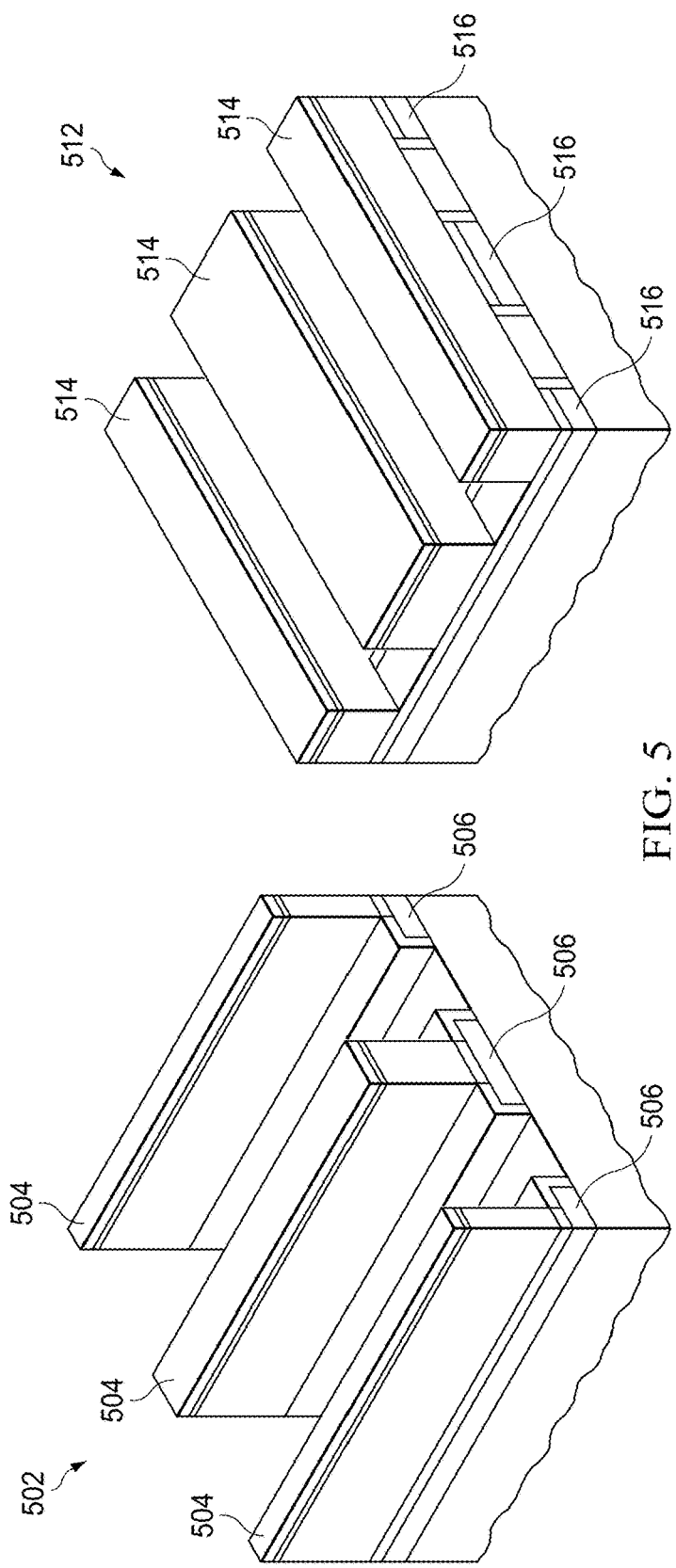
FIG. 5 illustrates a comparison of a collinear area shield and a perpendicular area shield according to this disclosure.

In some embodiments, instead of a collinear area shield, a perpendicular area shield can be implemented. For example, FIG. 5 illustrates a comparison of these two options. In FIG. 5, the structure 502 includes an area shield 504 with lines that are collinear with the sensing electrode fingers 506. This is analogous to the structure 300 with collinear area shield 412. In contrast, the structure 512 includes an area shield 514 with lines that are perpendicular to the sensing electrode fingers 516. In fact, many alternative area shield geometries can be considered; however a trade-off exists between shield efficacy and sensor sensitivity. For example, in some geometries, a reduction in size of the sensor area due to the presence of the area shield results in a decrease in sensitivity.

Figure 6:
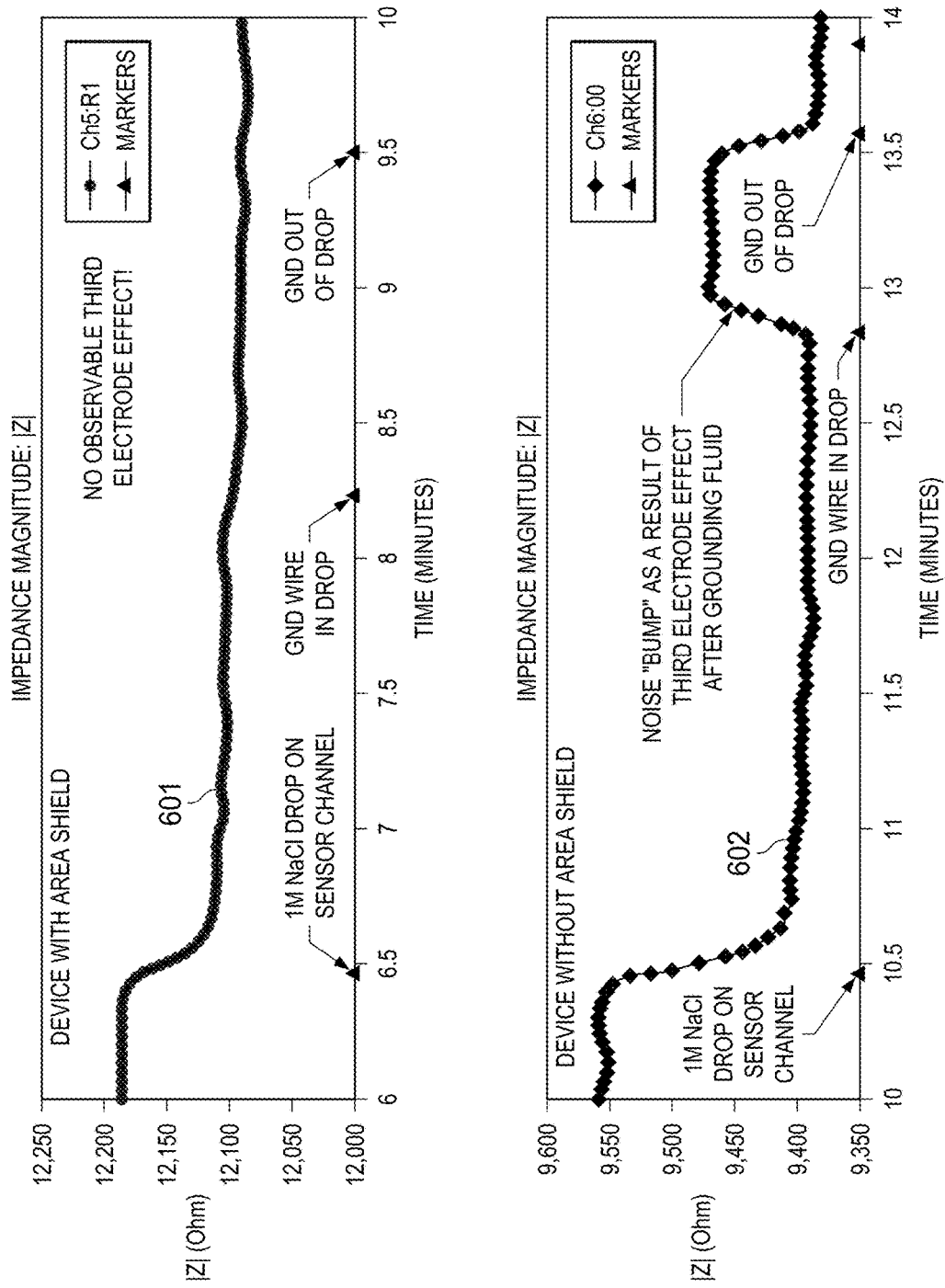
FIG. 6 illustrates experimental results that provide a comparison between use of a shielded sensing structure and use of a non-shielded sensing structure.
Figure 7A:
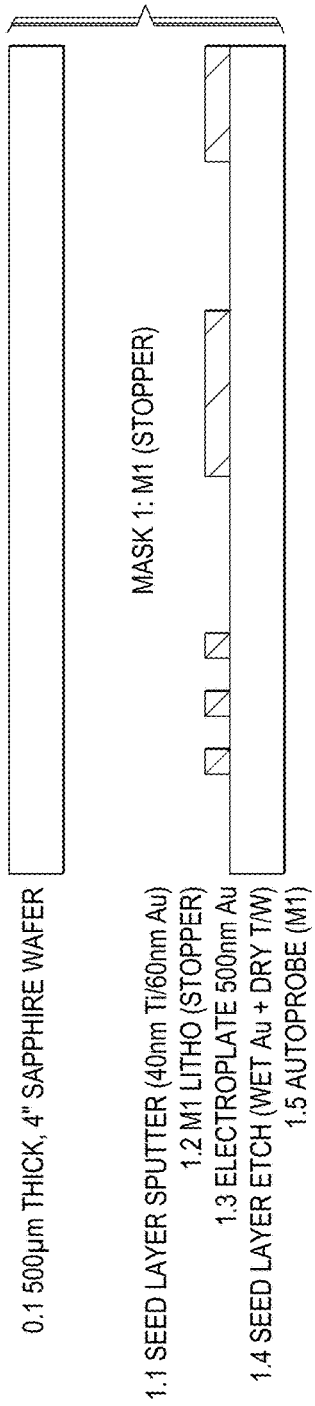
FIGS. 7A through 7F illustrate a schematic cross-sectional view of a thin film microfabrication process sequence used to produce a shielded sensing structure according to this disclosure.
Figure 7B:
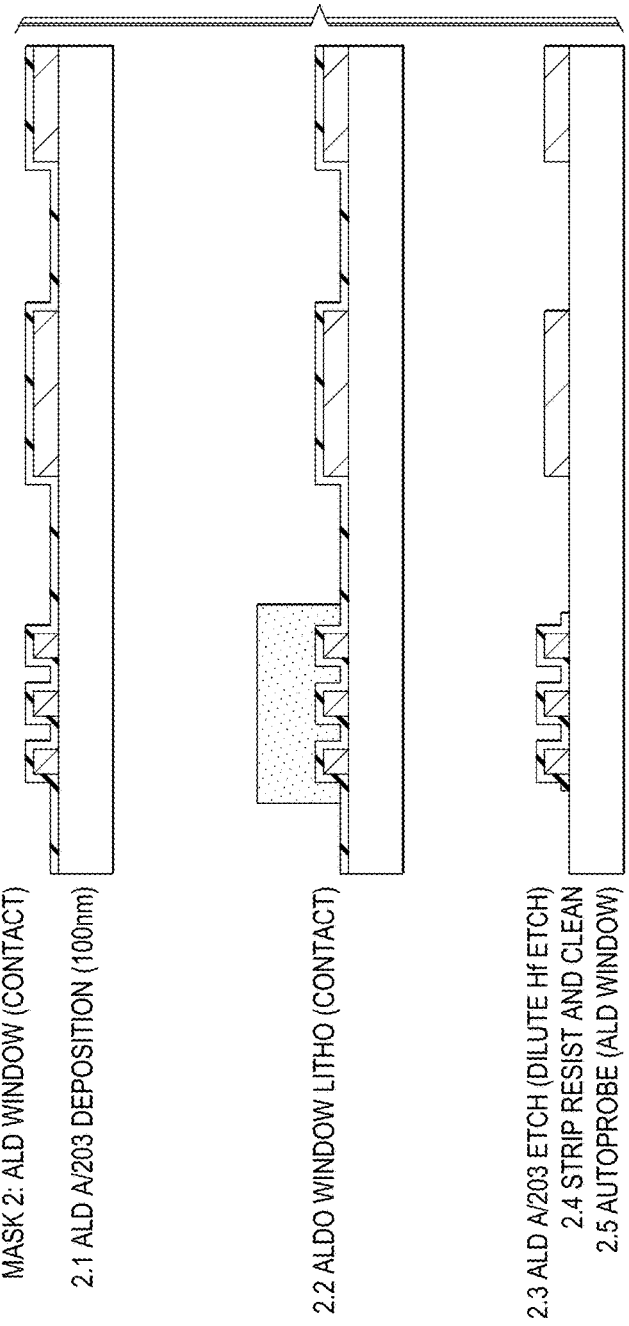
Figure 7C:
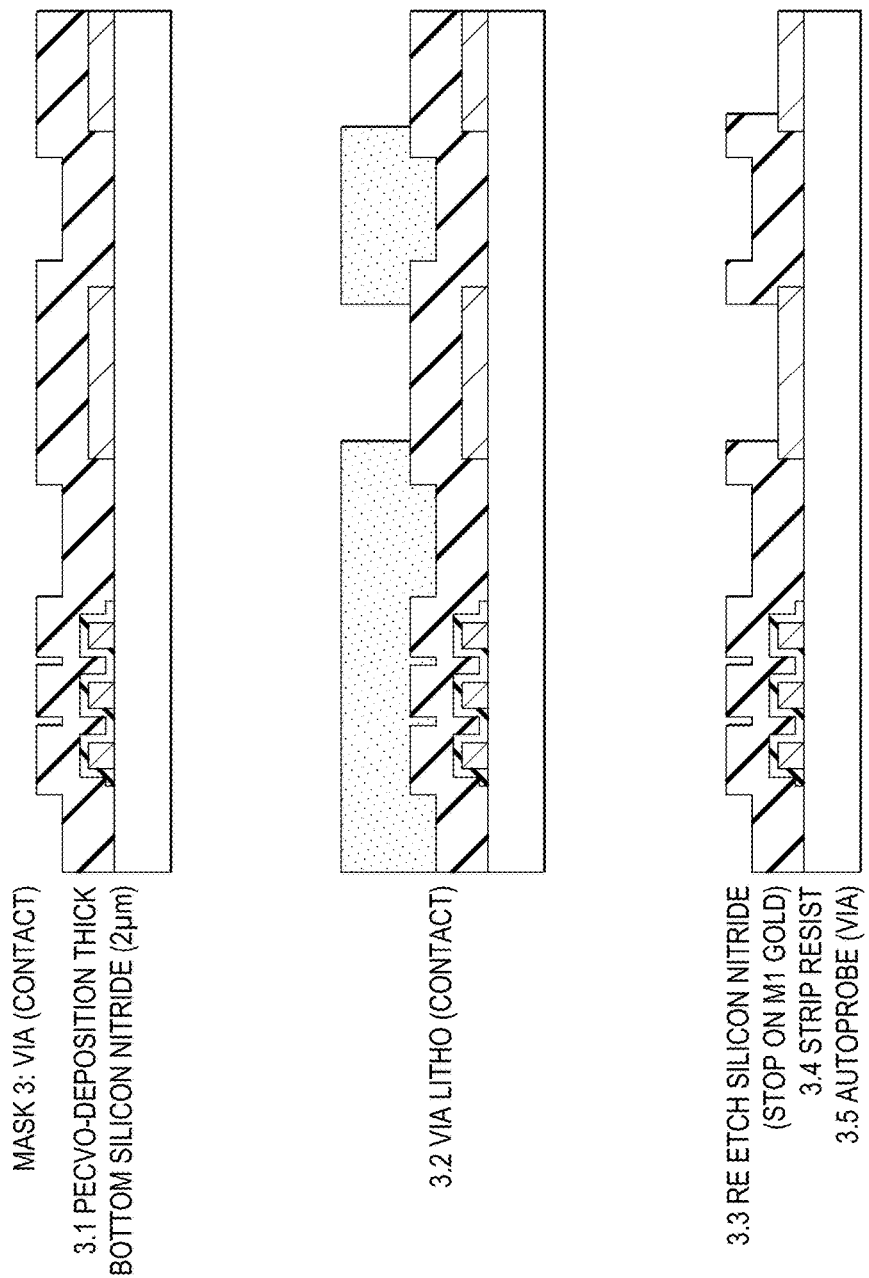
Figure 7D:
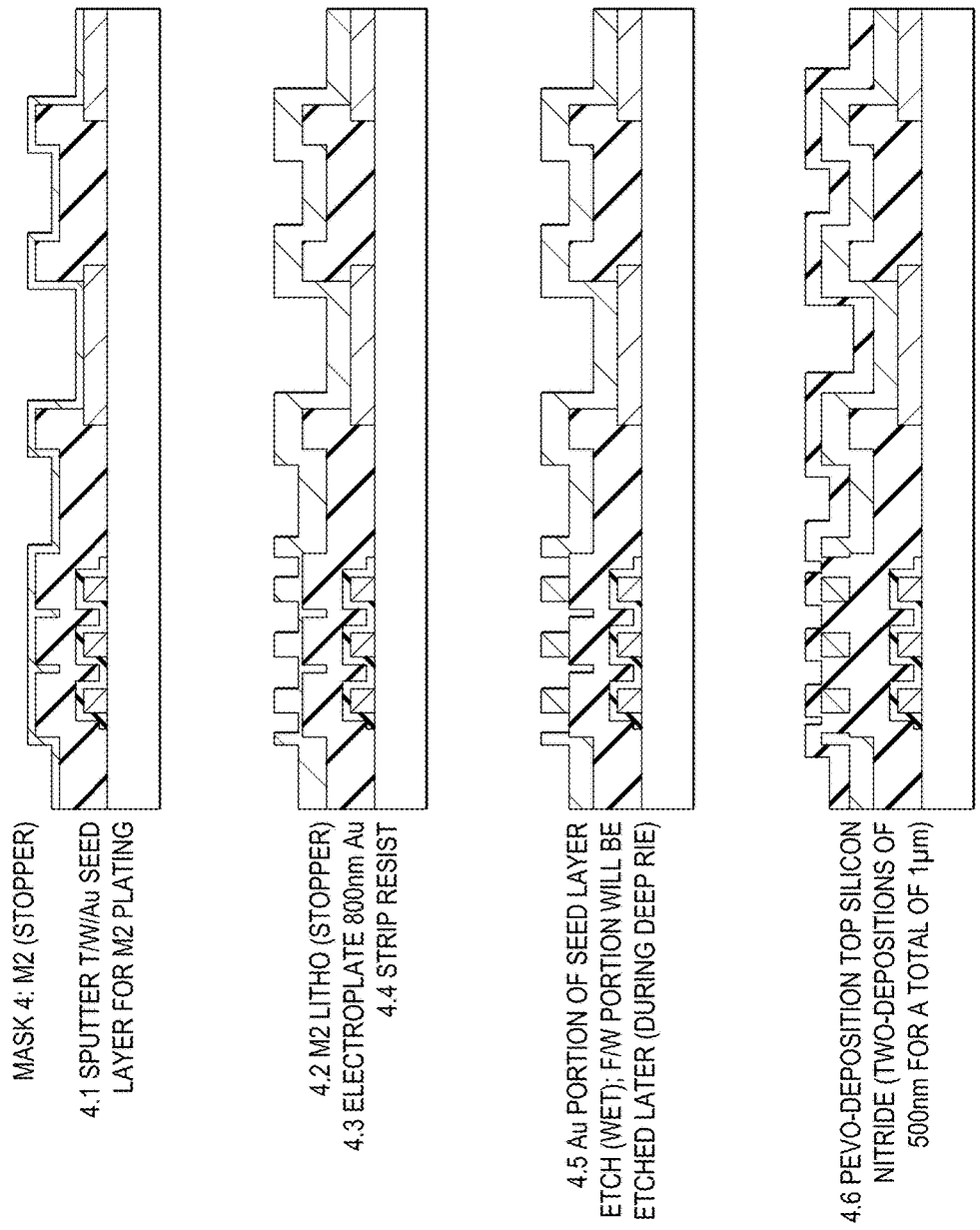
Figure 7E:
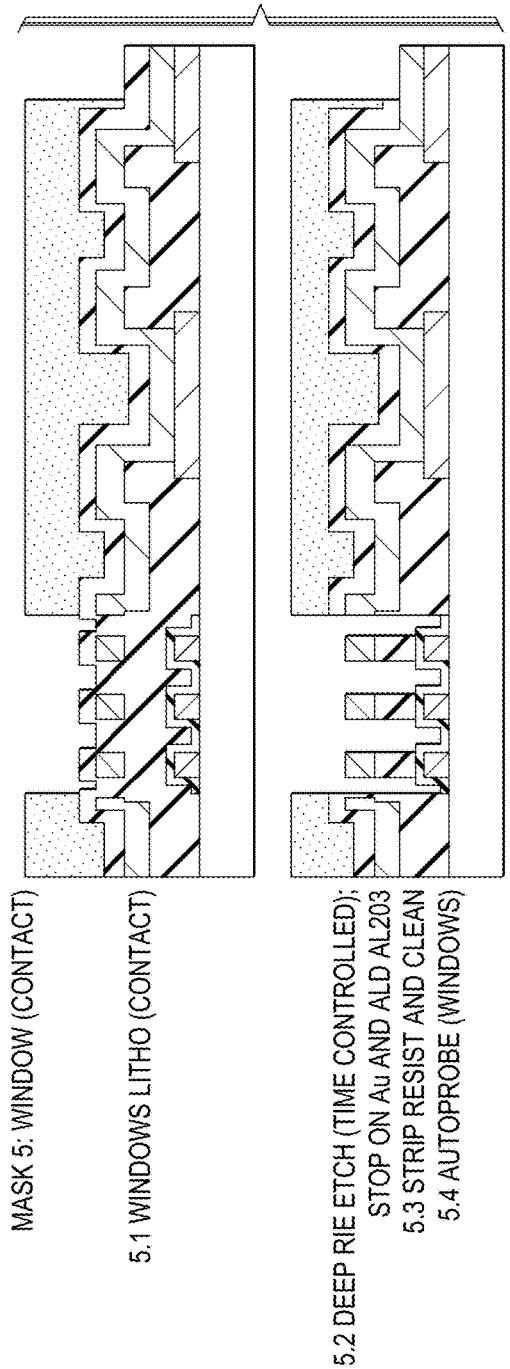
Figure 7F:
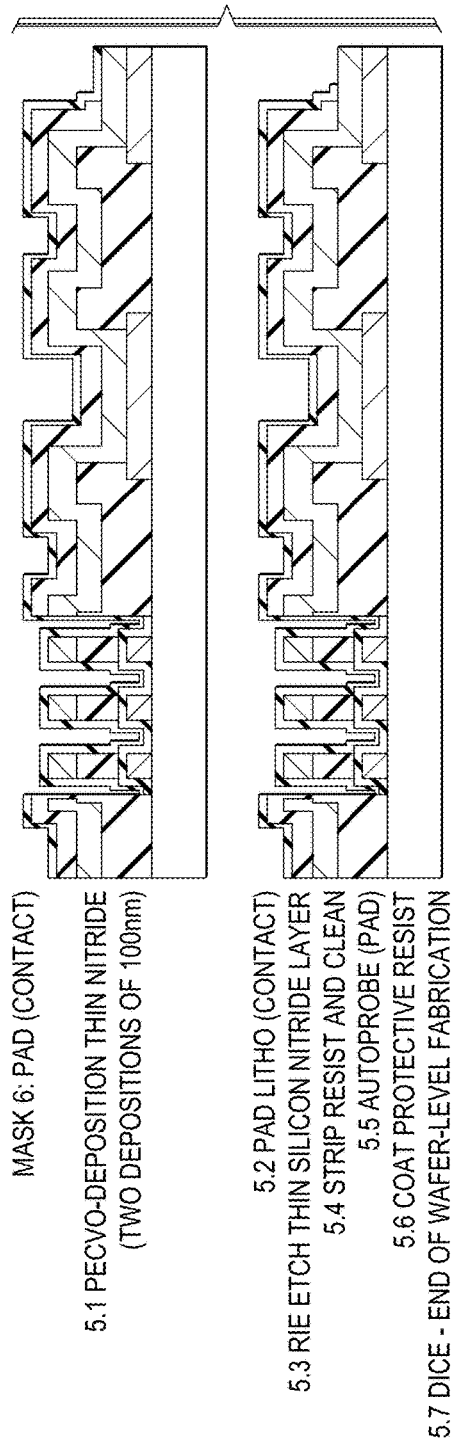

FIG. 6 illustrates experiment results that provide a comparison between use of a shielded sensing structure (such as depicted in FIG. 4E) and use of a non-shielded sensing structure. In the experiment, a drop of electrically conductive fluid is deposited onto the sensing area. Initially, the fluid is electrically floating. At a given time (marked by the box "GND wire in drop"), the fluid is electrically grounded by insertion of a wire. The two curves 601, 602 depict the response of the sensors over time. An ideal chemical sensor does not respond to a change in fluid voltage, only to a change in fluid composition. It can be seen that the shielded sensor behaves as such; the curve 601 does not change perceptibly when the fluid is grounded. However, in the signal of the non-shielded sensor, a spurious 'bump' appears in the curve 602 when the fluid potential changes.

In some embodiments, a shielded sensing structure, such as the sensing electrode structure 300 and electrical shielding system 400, can be produced using a thin film microfabrication process, such as depicted in FIGS. 7A through 7F.

FIGS. 7A through 7F illustrate a schematic cross-sectional view of a thin film microfabrication process sequence used to produce a shielded sensing structure according to this disclosure. In this process, the shielded sensing structure is disposed over a sapphire substrate by a first gold metallization layer ("M1") that forms the sensing electrode fingers 302, an inter-layer dielectric that includes approximately two microns of silicon nitride and that forms the dielectric layer 316, and a second gold metallization layer ("M2") that forms the area shield 412. The final structure is electrically passivated by a stack of thin conformal dielectric films (e.g., $Al_2O_3$ and silicon nitride). The sensing layer can deposited onto the inorganic substrate using a conformal spray-deposition process. Of course, this is merely one example process and is not limiting. Other processes could include other operations, other layers, and other materials.

RF-FLASh

Figure 8:
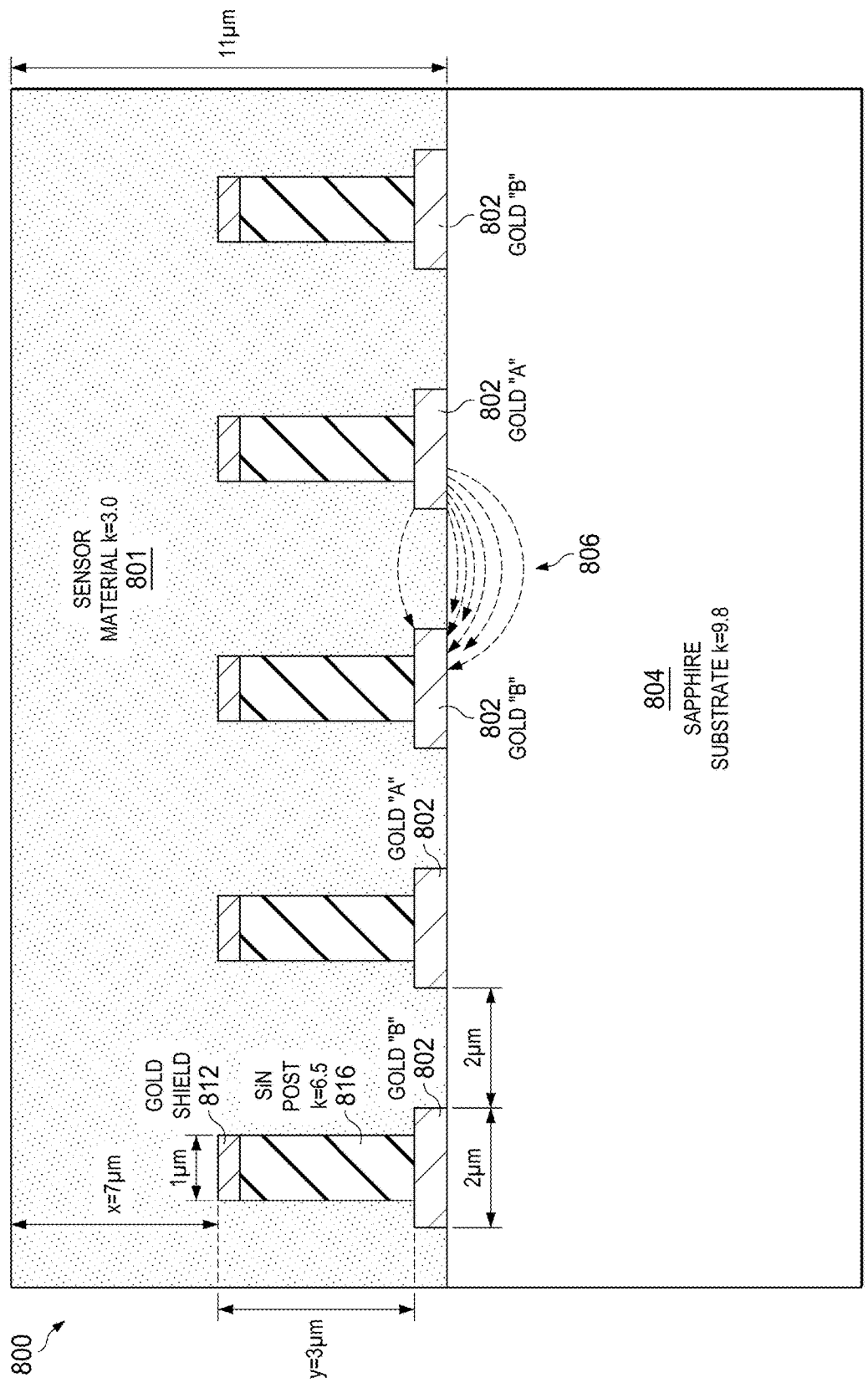
FIG. 8 illustrates details of another example FLASh sensor structure in which the sensor fingers lie directly on the substrate material according to this disclosure.

FIG. 8 illustrates details of another example FLASh sensor structure 800 according to this disclosure. The embodiment of the area-shielded sensor structure 800 shown in FIG. 8 is for illustration only. Other embodiments of the FLASh sensor structure 800 could be used without departing from the scope of this disclosure.

As shown in FIG. 8, the FLASh sensor structure 800 includes multiple M1 layer gold sensor electrode fingers 802 resting directly on a high dielectric constant (e.g., sapphire) substrate 804. A dielectric post 816 is disposed over each finger 802, and a portion of an area shield 812 is disposed over each dielectric post 816, similar to the structure shown in FIG. 4E. Sensing material 801 surrounds the fingers 802, posts 816, and shield 812. Having the M1 sensor electrode fingers 802 resting directly on the substrate 804 can lead to multiple issues: 1) Because the dielectric constant of the substrate 804 (k=9.8) and its protective dielectric layer(s) (not explicitly shown in FIG. 8) is so much larger than that of the sensing material 801 (k=3.0), the parasitic shunt capacitance between the M1 sensor electrode fingers 802 is relatively high. 2) For the same reason, very little of the sense field flux 806 between the M1 sensor electrode fingers 802 actually passes through the sensing material 801 itself; rather, most of the flux 806 is shunted through the substrate 804 and the protective dielectric layer(s) on the substrate 804, neither of which contributes to the actual chemical sensing function, thus resulting in reduced sensitivity. 3) The portion of the sensing material 801 that is sensed is primarily the very bottom of the sensing material 801 closest to the substrate 804, and in some cases, this may not be as high quality a material as the bulk sensing material 801 above.

Figure 9A:
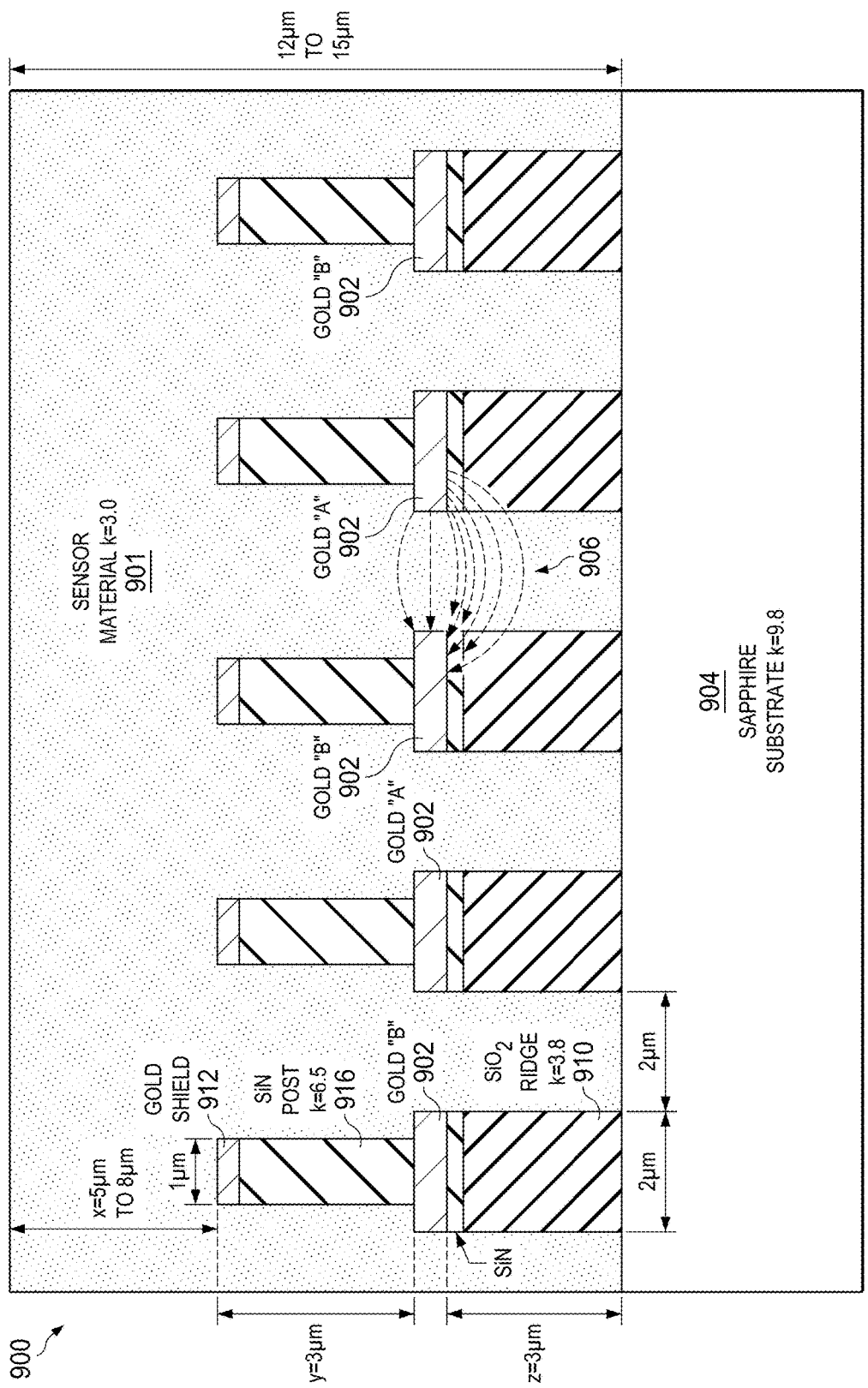
FIG. 9A illustrates details of an example Ridged-Finger Area-Shielded Fine-Line (RF-FLASh) sensor structure in which the sensor fingers are raised up on ridges, away from the substrate material, according to this disclosure.

FIG. 9A illustrates details of an example Ridged-Finger Area-Shielded Fine-Line (RF-FLASh) sensor structure 900 according to this disclosure. The embodiment of the RF-FLASh sensor structure 900 shown in FIG. 9A is for illustration only. Other embodiments of the RF-FLASh sensor structure 900 could be used without departing from the scope of this disclosure.

As shown in FIG. 9A, the RF-FLASh sensor structure 900 includes a number of components that are the same as, or similar to, the sensor structure 800 of FIG. 8. For example, the RF-FLASh sensor structure 900 includes a sensing material 901 that surrounds a plurality of M1 layer gold sensor electrode fingers 902. The fingers 902 are disposed over a high dielectric constant (e.g., sapphire) substrate 904 as in the FLASh configuration, but with the difference that, in the RF-FLASh configuration, the sensor fingers 902 are separated from the substrate 904 by ridges 910 of low dielectric constant material (such as $SiO_2$). A dielectric post 916 is disposed over each finger 902, and a portion of an area shield 912 is disposed over each dielectric post 916. While continuous ridges 910 of low dielectric material are shown in FIG. 9A, discontinuous pillars or other means to raise the fingers 902 off of the substrate 904 could be used without departing from the scope of this disclosure.

In some embodiments, each area shield 912 is formed of gold and is aligned over the center of the corresponding electrode finger 902. Each area shield 912 can be formed using projection lithography and is grounded as part of the same M2 plane that defines the lateral shields. In some embodiments, the dielectric posts 916 are silicon nitride (SiN) and are formed by anisotropic reactive ion etching using the projection patterned area shield 912 as a mask.

To address one or more of the issues identified in FIG. 8, the M1 electrode fingers 902 are raised up on ridges 910. The ridges 910 can be formed of silicon dioxide ($SiO_2$) and are formed by anisotropic reactive ion etching using the projection patterned electrode fingers 902 as a mask. The ridges 910 result in a separation of the electrode fingers 902 from the substrate 904. This separation, along with the low dielectric constant of $SiO_2$, reduces the parasitic capacitance through the substrate 904 and forces most of the electrostatic flux 906 from the "A" fingers to the "B" fingers to pass laterally through the sensor material 901, thereby increasing the electrostatic sensing efficiency and overall chemical sensitivity of the sensor structure 900.

While not explicitly shown in FIG. 9A, in some embodiments, a thin layer (e.g., 0.1 μm thickness) of protective dielectric can be included over some or all surfaces (e.g., electrodes, sapphire substrate, sidewalls, etc.). Note that FIG. 9A depicts a high, z=3 μm height for the ridges 910, this is merely one example and other values are possible. In some embodiments, the electrostatic efficiency is not seriously degraded at lower heights for the ridges 910, even down to z=1 μm to 2 μm. Similarly, although FIG. 9A depicts a height of the dielectric posts 916 of y=4 μm, this is merely one example and other values are possible. In some embodiments, good area shield performance can be obtained with post heights down to about y=2 μm, which also eases fabrication aspect ratio challenges.

In the sensor structure 900, by raising the M1 sensor electrode fingers 902 up on relatively low dielectric constant ridges 910 (e.g., $SiO_2$ with k=3.8), well above the substrate 904, the parasitic shunt capacitance is greatly reduced. Because the M1 electrode shunt path for flux down through the ridge 910, through the substrate 904, and up the adjacent ridge 910 is so tortuous, the vast majority of the electrostatic flux 906 passes directly across the lateral gap between the electrode fingers 902 through the sensor material 901, thereby greatly increasing the electrostatic efficiency and sensitivity of the sensor structure 900. Even if the quality of the sensor material 901 at the bottom (i.e., nearest the substrate 904) happens to be inferior, relative to the bulk, because the electrode fingers 902 are raised up on the ridges 910, the region of sensor material 901 being sensed should nominally be higher quality bulk material.

Thus, the RF-FLASh sensor structure 900 offers a significant improvement in sensitivity, while retaining all of the area shielding structures and capabilities of the sensor structures 300, 800, which allow the use of either insulating or conductive fluids with very low levels of direct electrostatic read-through. In addition, the basic substrate fabrication techniques used for the sensor structure 800 are still usable in the sensor structure 900, with the addition of an initial $SiO_2$ dielectric deposition and RIE (reactive ion etching) step after definition of the M1 fingers.

Figure 9B:
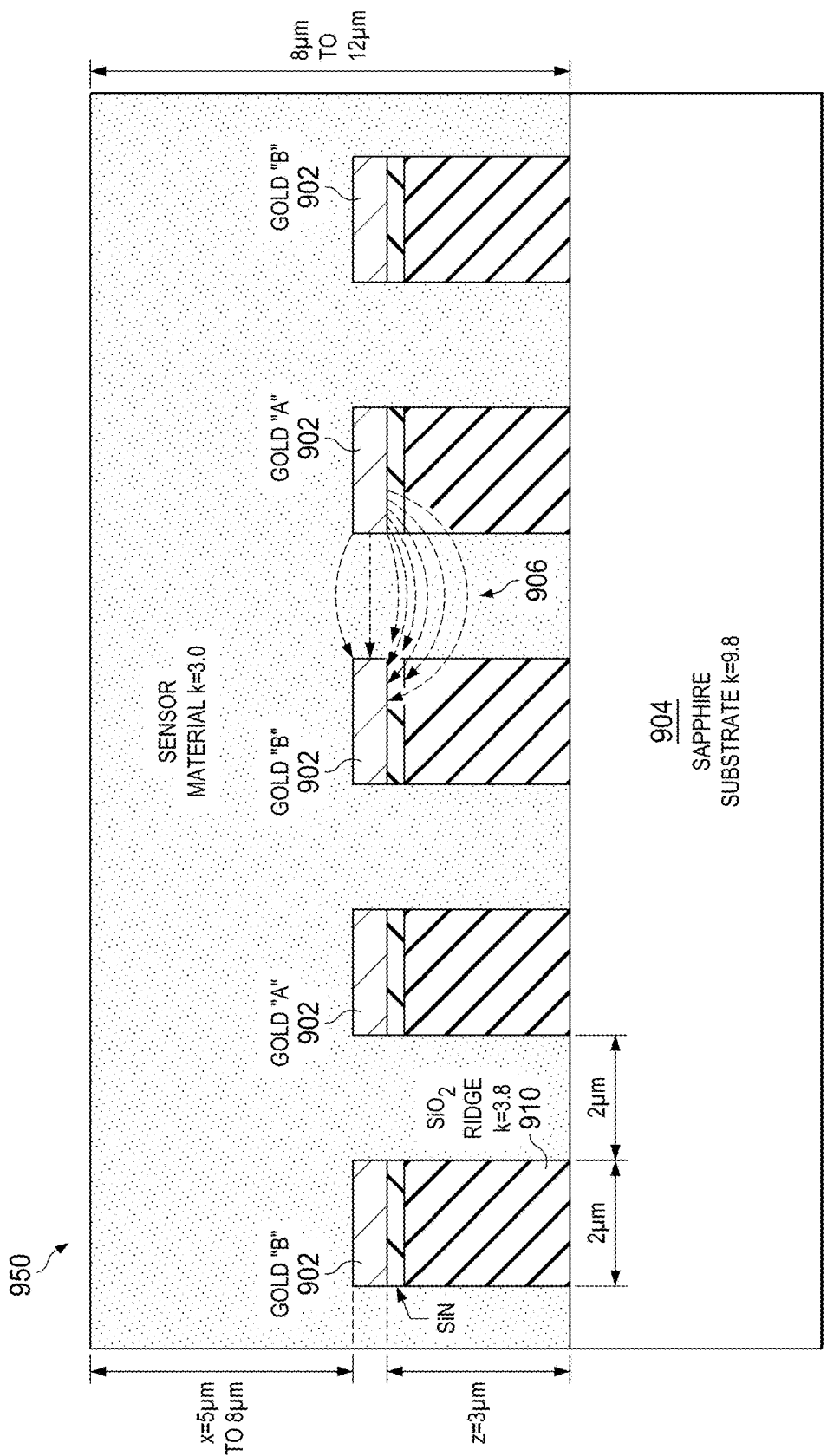
FIG. 9B illustrates a peripheral shield ridged finger fine line sensor structure that includes raised finger, but does not include area shielding, suitable for use with insulating fluids, according to this disclosure.

It is also noted that the ridged finger structure shown in FIG. 9A can be used with only a peripheral shield and no area shield. For example, FIG. 9B shows a ridged finger fine line sensor structure 950 that includes the low dielectric constant ridges 910 of FIG. 9A, but does not include the dielectric posts 816 and area shield 812 that are shown in FIG. 9A. This ridged finger peripheral shield (only) structure of FIG. 9B, while not offering the protection from the "third electrode effect" with conductive fluids of the RF-FLASh structure of FIG. 9A, when it is used with insulating fluids, it provides full "read-through" interference protection and the same advantages of lower sensor capacitance and very high electrostatic efficiency, and sensing of bulk (as opposed to near substrate) higher quality sensor material, of RF-FLASh, with a simpler fabrication process.

Comparison of Sensitivity of RF-FLASh to that of the FLASh

Two-dimensional (2D) electrostatic simulation results for the RF-FLASh sensor structure 900 and the FLASh sensor structure 800 can be compared to illustrate the differences between the two structures. In the simulations, an M1 interdigitated finger structure of 2 μm lines and 2 μm spaces was selected, lying directly on the sapphire substrate for the FLASh sensor structure 800 (FIG. 8), or raised up on 2 μm high $SiO_2$ ridges for the RF-FLASh sensor structure 900 (FIG. 9A). For purposes of these simulations, similar area-shield structures of 1 μm (or 1.6 μm) lines with 3 μm (or 2.4 μm) spacings on 3 μm (or 4 μm) high SiN posts were assumed (FIG. 8 and FIG. 9A), though a wider (2 μm lines and 2 μm spacings) top shield would give even higher performance, even with a lower SiN post height. In FIG. 8, the protective dielectric layers were not included, while in FIG. 9A, a 0.1 μm thickness was taken.

Figure 10:
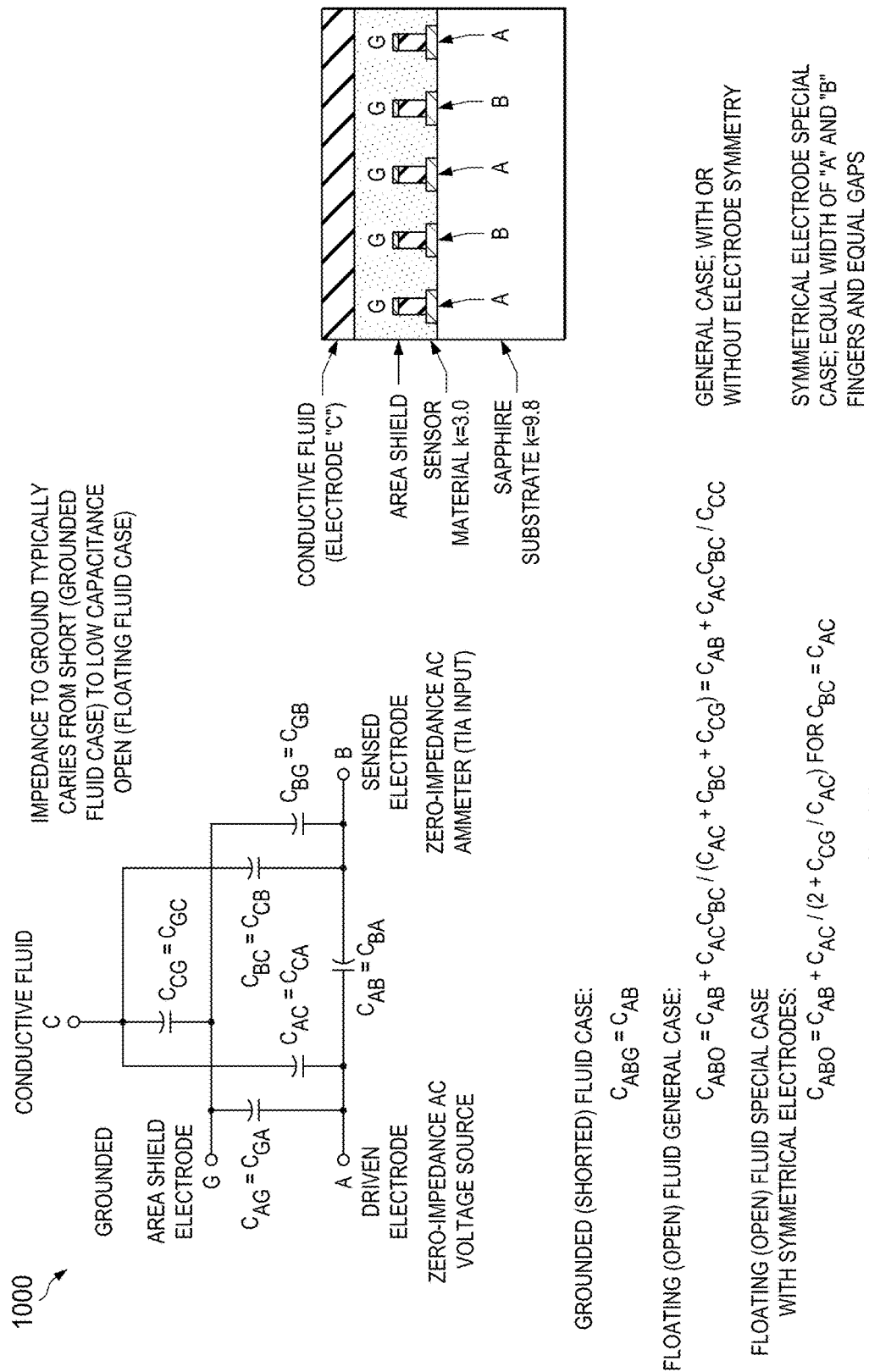
FIG. 10 illustrates a capacitance model obtained from a capacitance matrix for conductive fluid (3-electrode) two-dimensional (2D) field simulations of the RF-FLASh sensor structures of FIGS. 8 and 9A according to this disclosure.

FIG. 10 illustrates a capacitance model 1000 obtained from a capacitance matrix for the conductive fluid (3-electrode) 2D fields simulations of the RF-FLASh sensor structure 900 and the FLASh sensor structure 800 according to this disclosure. Note that while the capacitance matrix is defined for zero AC impedance on all electrodes, the capacitance model 1000 is applicable for any arbitrary impedances on the three ports. In normal operation, the "A" and "B" sensor finger electrode ports are operated at nominally zero impedance, while the conductive fluid "C" electrode (e.g., brine) might be either shorted to ground ($C_{ABG}$ case), floating ($C_{ABO}$ case), or with some other impedance to ground such as the capacitance of a long ground wire (possibly with someone holding it), or an overlapping brine drop experiment in which there is a capacitance to a lateral grounded shield. In all such cases, the measured response is calculated as a circuit problem given the various applied port impedances or capacitances.

FIGS. 11A through 11C illustrate the capacitance matrices obtained from 2D electrostatic simulations for the FLASh sensor structure 800 of FIG. 8 with k=3.00 and k=2.70 sensor material. The capacitance matrices for both simulations are shown to illustrate the change from k=3.00 sensor material to k=2.70 (−10% Δk). Note that, even with absolutely no protective SiN dielectric over the fingers 802, the electrostatic sensing efficiency (% change in $C_{AB}$/% change in k) is only 24.7%. Based on 2D simulations, with a 0.4 μm thick layer of SiN over the fingers 802 and substrate 804, this would drop by 40% to a 15% electrostatic sensing efficiency. The signal to noise ratio ("SNR") (i.e., the ratio of the change in $C_{AB}$ due to a 10% change in k to the change in $C_{AB}$ from floating to grounded fluid, $C_{ABO}-C_{ABG}$) is 34.56, due mainly to the 0.08% $C_{ABO}-C_{ABG}$ change.

The strong coupling between the M1 fingers 802 through the high-k (k=9.8) sapphire substrate 804 is illustrated in FIGS. 11A through 11C by the large magnitude of the capacitance between the "A" and "B" M1 sensor electrodes (e.g., $C_{AB}$~1,434 $pF/cm^2$, with k=3.00 sensor material). However, as shown in FIGS. 11A through 11C, in some implementations, the FLASh sensor structure 800 can exhibit low electrostatic sensing efficiency: 24.7% with no metal protection, and about 15% with a 0.4 μm SiN protective coating over the M1 electrode fingers 802 and the substrate 804. Much of the electrostatic flux is lost through unwanted parasitic substrate capacitance. The RF-FLASh sensor structure 900 of FIG. 9A, in which the M1 fingers 902 are raised up onto $SiO_2$ ridges, addresses this issue very effectively. The flux path from an "A" M1 finger 902 to a "B" electrode finger 902 would have to pass vertically through two low-k 2 μm $SiO_2$ (k=3.8) ridges 910, in series with the sapphire substrate 904 between the ridges 910, for a long, low k path. As illustrated in FIG. 9A, this effectively forces most of the applied AC flux 906 to pass directly laterally between the raised "A" and "B" M1 fingers 902, which means directly through the sensor material 901 (where the sensing actually takes place), instead of being shunted down through the sapphire substrate 904, greatly increasing the electrostatic efficiency.

FIGS. 12A through 12C illustrate the capacitance matrices obtained from 2D electrostatic simulation for the RF-FLASh sensor structure 900 of FIG. 9A (where again, the various capacitance matrix elements relate to the area-shielded fine-line sensor capacitance model of FIG. 10). One detail in the 2D simulated structure slightly different from FIG. 9A is that instead of straight-walled RIE etches, some undercut was assumed, such as starting with a grounded top shield of 1.6 µm lines and 2.4 µm spaces (instead of 1.0 µm/3.0 µm as in FIG. 8), with the SiN post tapering to 1.0 µm. The narrower, 2.4 µm shield gaps improve the capacitance shift from grounded conductive fluid to floating to an impressive 0.0035% (a 23× improvement over the 0.08% in FIG. 8). The effectiveness of raising the M1 sensor electrode fingers 902 up onto the $SiO_2$ ridges 910 is immediately apparent from the observed high electrostatic efficiency, 68.4% (with 0.1 µm of SiN protecting the electrodes, up from 24.7% shown in FIGS. 11A through 11C with no protection, or 15% with 0.4 µm of SiN protection), and the reduced sensor capacitance $C_{AB}$=923.6 pF/cm$^2$ with the RF-FLASh sensor structure 900, as compared to $C_{AB}$=1434 pF/cm$^2$ for the FLASh sensor structure 800. The "SNR" is increased to "SNR"=2336, which is approximately 68 times the "SNR"=34.56 result in FIGS. 11A through 11C.

Dimensional Scaling of the RF-FLASh to Further Improve Speed of Response and Sensitivity.

The simulated performance (shown in FIGS. 12A through 12C) of the nominal 2 µm lines and spaces in the RF-FLASh sensor structure 900 shown in FIG. 9A is excellent, and clearly indicates the performance advantages to be realized by raising the M1 fingers 902 up on the $SiO_2$ ridges 910.

It is also possible to affect the response time of the chemical sensor due to changes in analyte composition at the interface between the sensor material and the fluid (shown specifically as electrode "C" in the inset in FIG. 10, or implicitly as that which lies above the top of the sensor material 801, 901 in FIGS. 8 and 9A). The detailed transient response of the chemical sensors to changes in applied analyte composition can be complex and dependent on subtleties of various diffusion and other physical/chemical mechanisms in the sensor materials/structure. However, as a rough indication of the expected variation of response time with key physical dimensions (e.g., sensor layer thickness), the assumption of simple, Fick's law, diffusion is useful. With simple, Fick's law, diffusion, the response time goes nominally as the square of the layer thickness through which the diffusion takes place (e.g., the 11 µm thickness of the sensor material 801 in FIG. 8, or roughly the x+y=12 µm thickness of the sensor material 901 from the surface to the M1 fingers 902 in FIG. 9A).

If it were considered important to quadruple the speed of response of the chemical sensors, then it should be possible to achieve that 4× reduction of response time by halving the thickness of the chemical sensor layers. This 2× downscaling of the chemical sensor layer thickness could nominally be accomplished without disturbing the electrostatic effectiveness of the area shield structure, etc., by dropping the M1 sensor finger pitch from 2 µm lines and spaces down to 1 µm lines and spaces, with other dimensions scaled accordingly. While fabrication of 1 µm M1 lines and spaces with acceptable yields has proven challenging in earlier M1 finger directly on sapphire substrate designs, when the M1 fingers are raised up on the $SiO_2$ ridges, it may be possible (using suitable RIE tools) to achieve adequate yields with 1 µm M1 lines and spaces.

FIGS. 13A through 13C illustrate capacitance matrices obtained from 2D electrostatic simulations for a RF-FLASh sensor structure with reduced geometry (1 µm M1 lines and 1 µm spaces) compared to what is shown in FIG. 9A. That is, the structure used in the simulation of FIGS. 13A through 13C is similar to the RF-FLASh sensor structure 900 of FIG. 9A, except that the widths of, and gaps between, the "A" and "B" fingers 902 is reduced from 2.0 µm to 1.0 µm. The area shield 912, and hence the top of the SiN posts 916, is kept at a 1.0 µm width, but a gradual undercut or taper going down below the shield level is assumed so that the bottom half of the SiN post is 0.6 µm wide. While a z=3.0 µm height of the $SiO_2$ ridge 910 was simulated, a z=1.5 µm $SiO_2$ ridge height would have given virtually identical results. Also, while a y=3.0 µm height of the SiN post 916 was simulated here, a y=2.0 µm post height would have performed nearly as well. For protection from well fluids, a 100 nm thick $Al_2O_3$ coating around all metal electrodes (and the SiN and $SiO_2$ dielectric walls) was assumed in the analysis. Such protective coatings can be deposited using ultra-conformal thin film deposition techniques like ALD (Atomic Layer Deposition). However, like the z and y dimensions, these additional coatings do not change the mask layout (nor does the sensor material thickness of x=5.0 µm above the shield top).

In FIGS. 13A through 13C, the capacitance (C/A in pF/cm$^2$) matrix results for normal k=3.00 and 10% reduced k=2.70 sensor materials are shown. While the electrostatic efficiency of 68.36% is unchanged from the 2 µm lines and spaces case of FIGS. 12A through 12C, the change in capacitance when the sensor k is reduced 10% from k=3.00 to k=2.70 is very large: s$\Delta C_{AB}$=178.9 pF/cm$^2$/10% $\Delta$k, as compared to 21.2 pF/cm$^2$/10% $\Delta$k for the 2 µm/2 µm FLASh with 0.4 µm protective dielectric or 35.4 pF/cm$^2$/10% $\Delta$k with no protective dielectric (as shown in FIGS. 11A through 11C).

There are a number of important observations from a review of the 2D field simulation results of FIGS. 13A through 13C for the 1 µm/1 µm RF-FLASh sensor structure. The electrostatic sensing efficiency (ESE) is 68.36%, essentially unchanged from the ESE=68.37% for the 2 µm/2 µm RF-FLASh case of FIGS. 12A through 12C, and much higher than the 24.7% ESE in FIG. 10 for no metal protection or ESE=15% with 0.4 µm SiN metal protection layer. Because with the 1 µm/1 µm line/space pitch, twice as much finger length is included into the same sensor area as with the more relaxed 2 µm/2 µm line/space geometry, the capacitances are all larger. The big change for the 1 µm/1 µm RF-FLASh sensor is that the absolute sensitivity (i.e., the change in $C_{AB}$ for a 10% change in k) is increased to s$\Delta C_{AB}$=178.9 pF/cm$^2$/10% $\Delta$k, which is up by 8.4× from about 21.2 pF/cm$^2$/10% $\Delta$k for the FLASh with 0.4 µm SiN metal protection layer, or for the FLASh with no protective dielectric, 35.4 pF/cm$^2$/10% $\Delta$k (FIGS. 11A through 11C, for 2 µm/2 µm with fingers directly on sapphire), or up by 2.83× from the 63.15 pF/cm$^2$/10% $\Delta$k with the 2 µm/2 µm RF-FLASh case.

There is an increase in the sensor line loading capacitance, $C_{BB}$=3299.35 pF/cm$^2$ for the 1 µm/1 µm RF-FLASh, versus the $C_{BB}$=2052.7 pF/cm$^2$ for the 2 µm/2 µm FLASh or the $C_{BB}$=1207.35 pF/cm$^2$ for the 2 µm/2 µm RF-FLASh, but the modest increase in voltage noise-induced current noise in the TIA sense circuitry should be dwarfed by the much larger signal. As a sensor substrate layout issue, however, it should be noted that with the increased $C_{AA}$ and $C_{BB}$ loading capacitances in a 1 µm lines and spaces design, it becomes important to reduce the feed line resistances (now typically 10 ohms per line, or 20 ohms per sensor) in order to keep from adding voltage noise at the TIA input. One way to reduce these feed line resistances is by adding thicker plating to the feed line (and pad) areas of the M1 metallization.

Another important observation in the 1 µm/1 µm RF-FLASh sensor is that the change in $C_{AB}$ from grounded to floating conductive fluid in FIGS. 13A through 13C is a remarkably small 0.00018%, which gives an "SNR" value (the ratio of the change of $C_{AB}$ due to a −10% change in sensor k to the change of capacitance in going from a grounded fluid to a floating fluid) of "SNR"=44,026.69 for the 1 μm/1 μm RF-FLASh, up from "SNR"=35.56 with the 2 μm/2 μm FLASh (as shown in FIGS. 11A through 11C). Another way of looking at this very high "SNR" result is that the efficiency of the area shield structure is very high. The height of the SiN posts supporting the area shield could be reduced from its y=3.0 μm value used in FIGS. 13A through 13C down to about y=2.0 μm, and the sensor layer thickness above the area shield electrodes could be reduced from x=5 μm to about x=4 μm while maintaining high electrostatic performance. That would reduce the thickness of sensor material above the M1 sensor fingers to about x+y=6 μm for this 1 μm/1 μm geometry, which value is about half of the x+y=12 μm sensor layer thickness from the fluid-sensor interface to the M1 fingers for the 2 μm/2 μm RF-FLASh case in FIG. 9A. As per the earlier discussion, this would, for Fick's law diffusion, give about a 4× faster response time for the 1 μm/1 μm sensor geometry than for a 2 μm/2 μm scaling.

Figure 14:
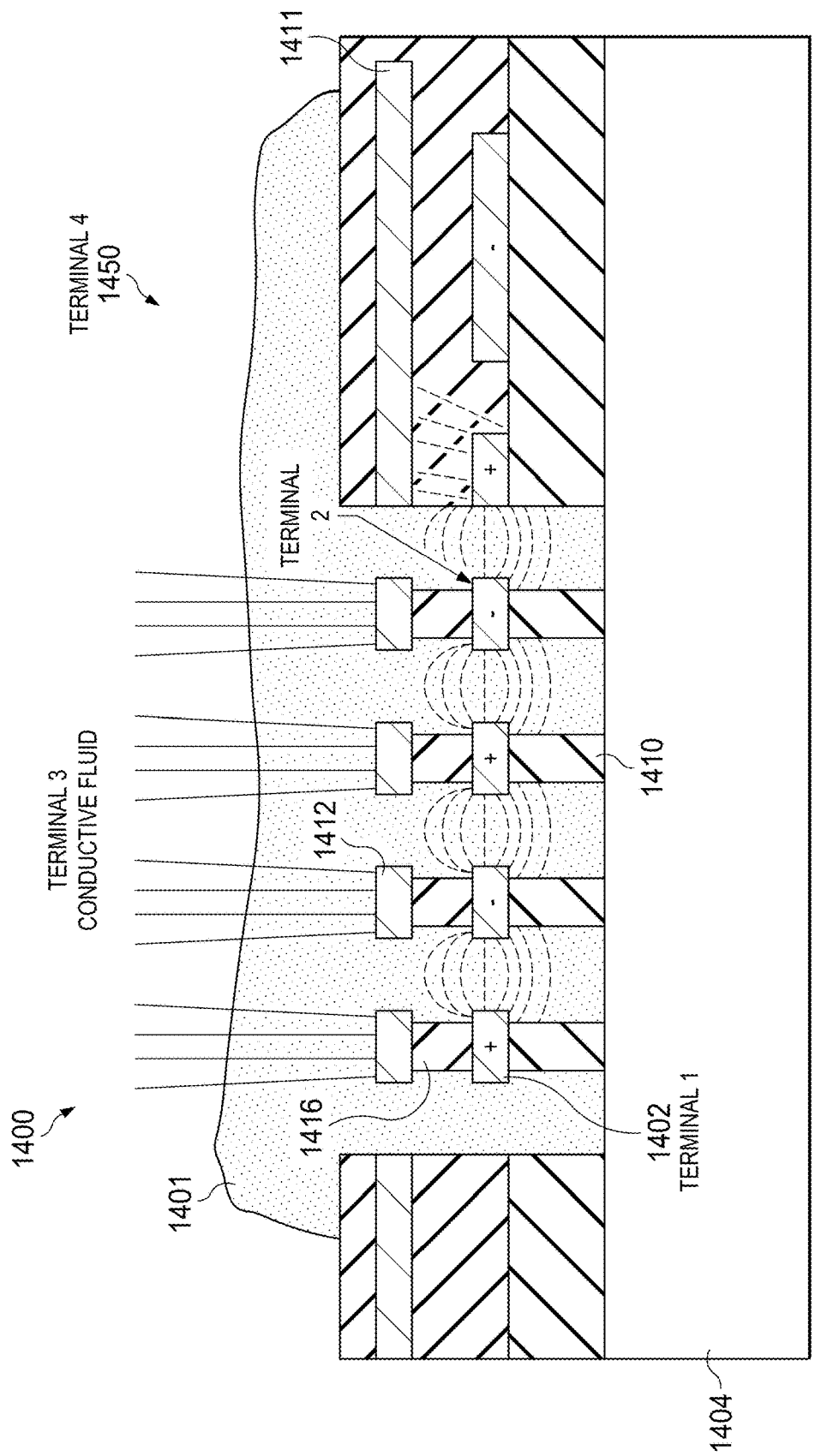
FIG. 14 illustrates details of another example RF-FLASh sensor structure according to this disclosure.

FIG. 14 illustrates details of another example RF-FLASh sensor structure 1400 according to this disclosure. The embodiment of the RF-FLASh sensor structure 1400 shown in FIG. 14 is for illustration only. Other embodiments of the RF-FLASh sensor structure 1400 could be used without departing from the scope of this disclosure.

As shown in FIG. 14, the RF-FLASh sensor structure 1400 includes a number of components that are the same as, or similar to, the RF-FLASh sensor structure 900 of FIG. 9A. For example, the RF-FLASh sensor structure 1400 includes a sensing material 1401 that surrounds a plurality of M1 layer gold sensor electrode fingers 1402. The fingers 1402 are raised up on ridges 1410 of low dielectric constant material that rest directly on a high dielectric constant (e.g., sapphire) substrate 1404. A dielectric post 1416 is disposed over each finger 1402, and a portion of an area shield 1412 is disposed over each dielectric post 1416. In addition, the RF-FLASh sensor structure 1400 includes a peripheral shield 1411 that is the same as, or similar to, the peripheral shield 310 of FIGS. 3A and 4E, and present in the structure (but outside the region illustrated) in FIGS. 8 and 9A. Together, the peripheral shield 1411 and the area shield 1412 form a shielding system 1450, analogous to the shielding system 400 of FIG. 4E.

The peripheral shield 1411 is only shown on the right and left sides of the sensor finger array in FIG. 14. In actual practice, as illustrated in FIG. 3A, the peripheral shield 310, 1411 can completely surround the entire array, covering the edges of the sensor finger area, the common connection electrodes into which the "A" and "B" sensor fingers (302 in FIG. 3A) attach, and the feed lines from these to the "A" and "B" pads (306 and 308 in FIG. 3A) that lie within, and somewhat beyond, the "sensing environment" shown in FIG. 3A.

VRF-FLASh

In the FLASh sensor structures of FIGS. 4E and 8, it can be seen that a large portion of the electric field generated between stimulus and sense electrodes flows through the substrate rather than through the sensing material (the ratio is determined by the ratio of dielectric constants, and the sapphire substrate typically used has a significantly larger k than the sensing material, resulting in a bigger portion of the field penetrating it). This portion of the field may not be utilized by the sensor, and will appear as a relatively large parallel or shunt capacitance (as measured between terminals 1 and 2). In the RF-FLASh sensor structures of FIGS. 9A and 14, most of the field lines will flow through the sensing material, resulting in a higher electrostatic efficiency and a significant increase in sensor response.

Figure 15:
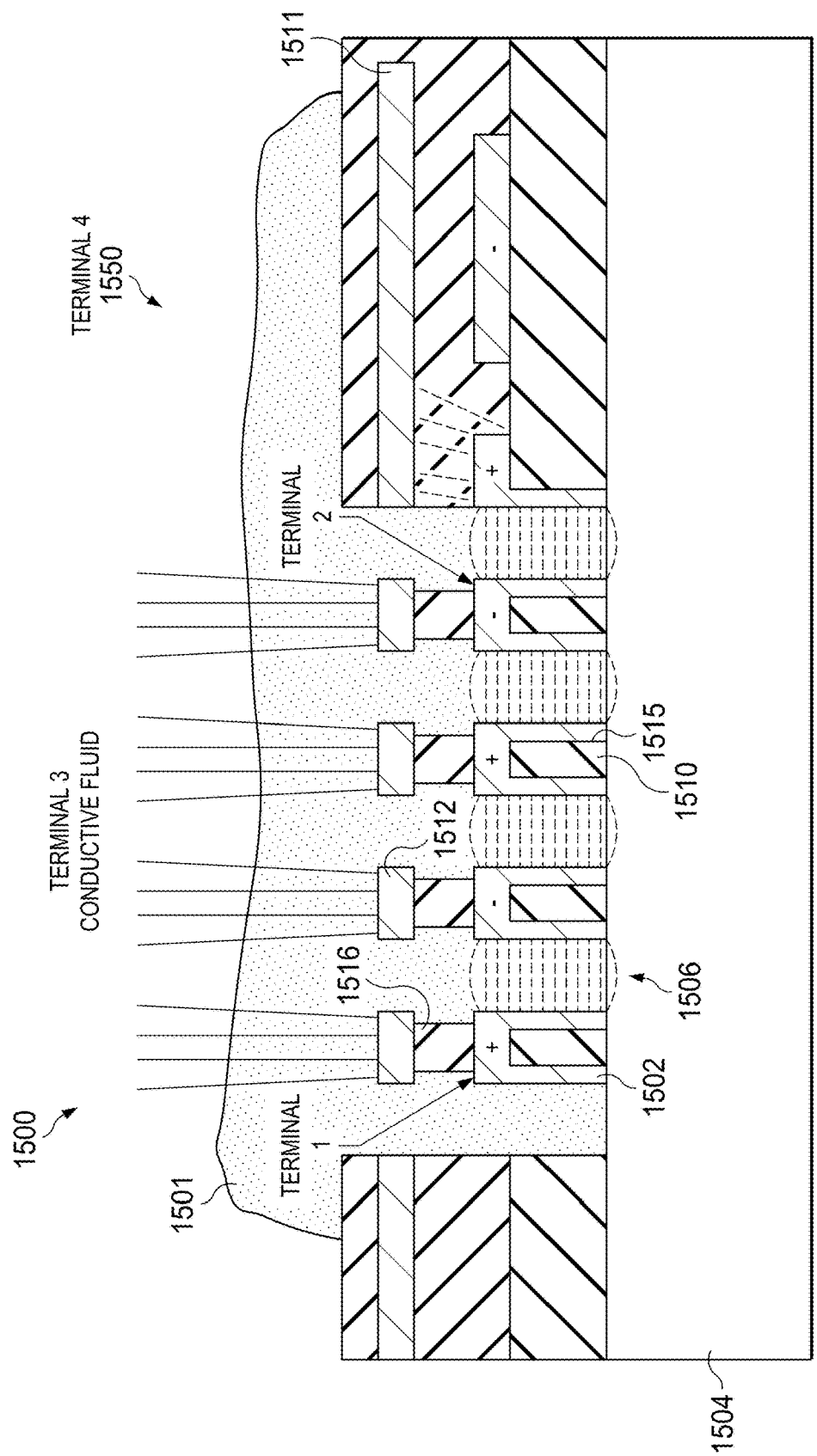
FIG. 15 illustrates details of an example Vertical-electrode Ridged-Finger Area-Shielded Fine-Line (VRF-FLASh) sensor structure according to this disclosure.

FIG. 15 illustrates details of an example Vertical-electrode Ridged-Finger Area-Shielded Fine-Line (VRF-FLASh) sensor structure 1500 according to this disclosure. The embodiment of the VRF-FLASh sensor structure 1500 shown in FIG. 15 is for illustration only. Other embodiments of the VRF-FLASh sensor structure 1500 could be used without departing from the scope of this disclosure.

The VRF-FLASh sensor structure 1500 represents a modification of the RF-FLASh fabrication process to achieve a different sense electrode shape, at the expense of higher parasitic capacitance and somewhat lower electrostatic efficiency, as compared to the RF-FLASh sensor structure 1400 of FIG. 14. As shown in FIG. 15, the VRF-FLASh sensor structure 1500 includes a number of components that are the same as, or similar to, the RF-FLASh sensor structure 1400. For example, the VRF-FLASh sensor structure 1500 includes a sensing material 1501 that surrounds a plurality of M1 layer gold sensor electrode fingers 1502. The fingers 1502 are disposed over a high dielectric constant (e.g., sapphire) substrate 1504. A dielectric post 1516 is disposed over each finger 1502, and a portion of an area shield 1512 is disposed over each dielectric post 1516. The VRF-FLASh sensor structure 1500 also includes a peripheral shield 1511 that is the same as, or similar to, the peripheral shield 1411 of FIG. 14. Together, the peripheral shield 1511 and the area shield 1512 form a shielding system 1550, analogous to the shielding system 1450 of FIG. 14.

As in the RF-FLASh sensor structure 1400 of FIG. 14, the VRF-FLASh sensor structure 1500 includes ridges 1510 that rest directly on the substrate 1504. Unlike the RF-FLASh, in the VRF-FLASh sensor structure 1500, the ridges 1510 elevate only the top of the "A" and "B" sensor electrode fingers 1502 away from the substrate 1504. In addition, each ridge 1510 includes vertical sidewalls 1515 that are coated with a conductive material that is formed integrally with the corresponding electrode finger 1502, thereby forming a "Π" electrode shape that is not elevated from the substrate 1504. Thus, in the VRF-FLASh sensor structure 1500, the conductive surface of the electrode finger 1502 extends across the top of the ridge 1510 and also down the sidewalls 1515 of the ridge 1510, forming the "Π" electrode shape.

Because the Π-shaped electrodes 1502 sit directly on the high dielectric constant sapphire substrate 1504, substantial parasitic flux will pass directly through the substrate 1504, so the parasitic substrate capacitance is higher, and the electrostatic efficiency somewhat lower than for the RF-FLASh sensor structure 1400. However, while the increased parasitic substrate capacitance is essentially the same as for the FLASh sensor structure 800, the electrostatic efficiency is much better than the FLASh sensor structure 800 because in the VRF-FLASh sensor structure 1500, that parasitic substrate capacitance represents a much lower fraction of the total sensed capacitance. This is illustrated in FIG. 15, which shows most of the flux field lines 1506 perpendicularly terminating on vertical sidewalls 1515. As a result, a good percentage of the flux field lines 1506 are contained within the sensing material 1501, and in particular are mostly contained in the narrow, high-aspect ratio gap between the ridges 1510 and run horizontally, rather than fringe out as in the sensing electrode structure 300 of FIG. 4E and the RF-FLASh sensor structure 1400 of FIG. 14. The result is a higher field line density and larger sensed capacitance, and, even though the VRF-FLASh electrostatic efficiency is not quite as high as the RF-FLASh, it is much higher than that of the FLASh structure.

FIG. 16 illustrates field simulation results that compare the VRF-FLASh design of FIG. 15 to the RF-FLASh design of FIG. 14 for a set of design parameters (1 µm and 2 µm linewidths, a 3 µm ridge height in all cases, a 3 µm shield post height for 1 µm linewidth/4 µm shield post height for 2 µm linewidth, a 5 µm sensing material thickness for 1 µm linewidth and 8 µm sensing material thickness for 2 µm linewidth). As indicated, FIG. 16 includes results created by 2D simulations as well as 3D simulations. As can be seen in the column displaying the predicted sensor response (expressed as the capacitance change in pF/cm$^2$, for a change of 10% in the dielectric constant of the sensing material, k=3 to 2.7), the improvement in sΔCAB is significant.

Figure 17A:
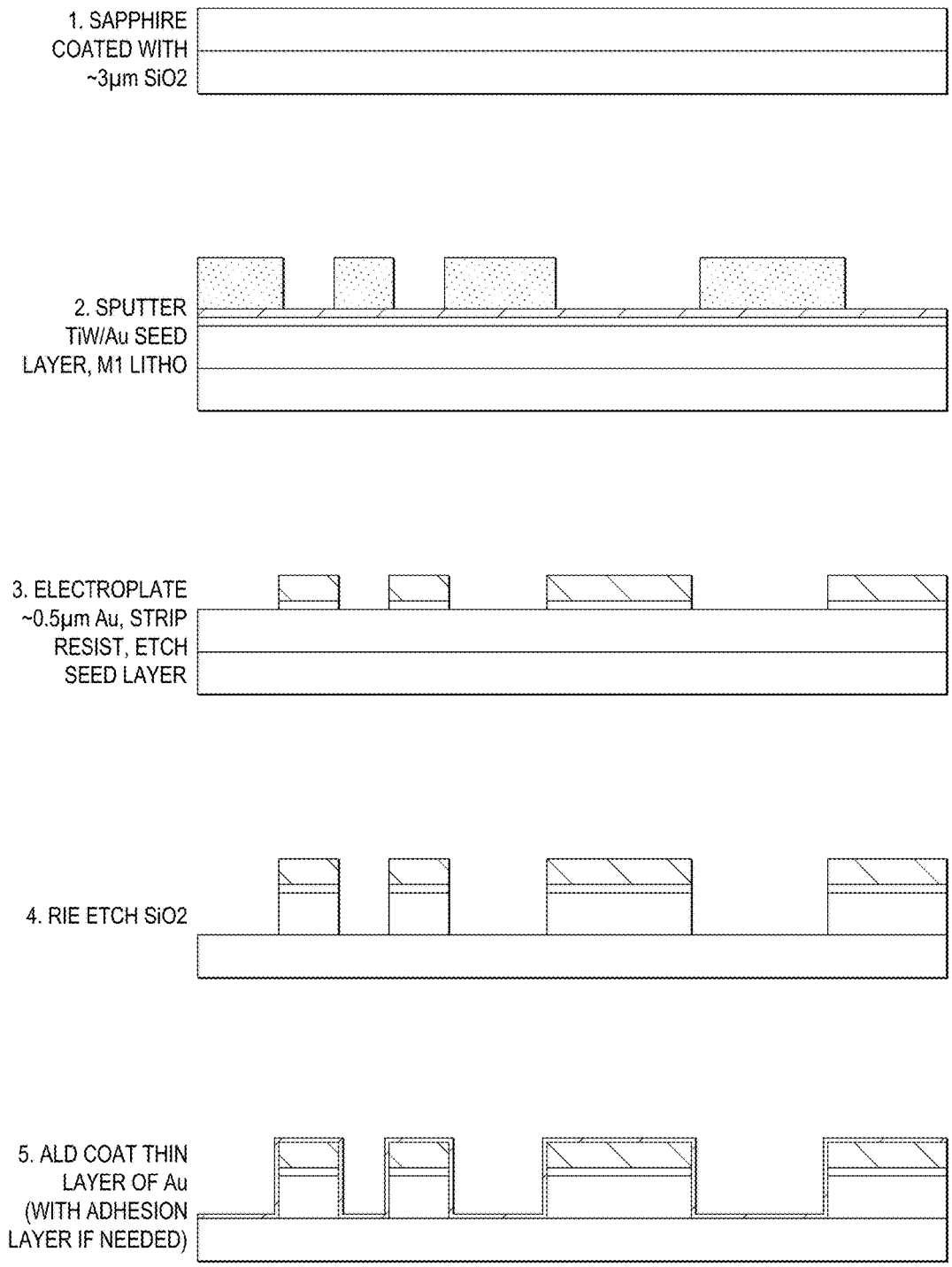
FIGS. 17A, 17B, and 18 illustrate microfabrication processes to produce the VRF-FLASh sensor structure of FIG. 15.
Figure 17B:
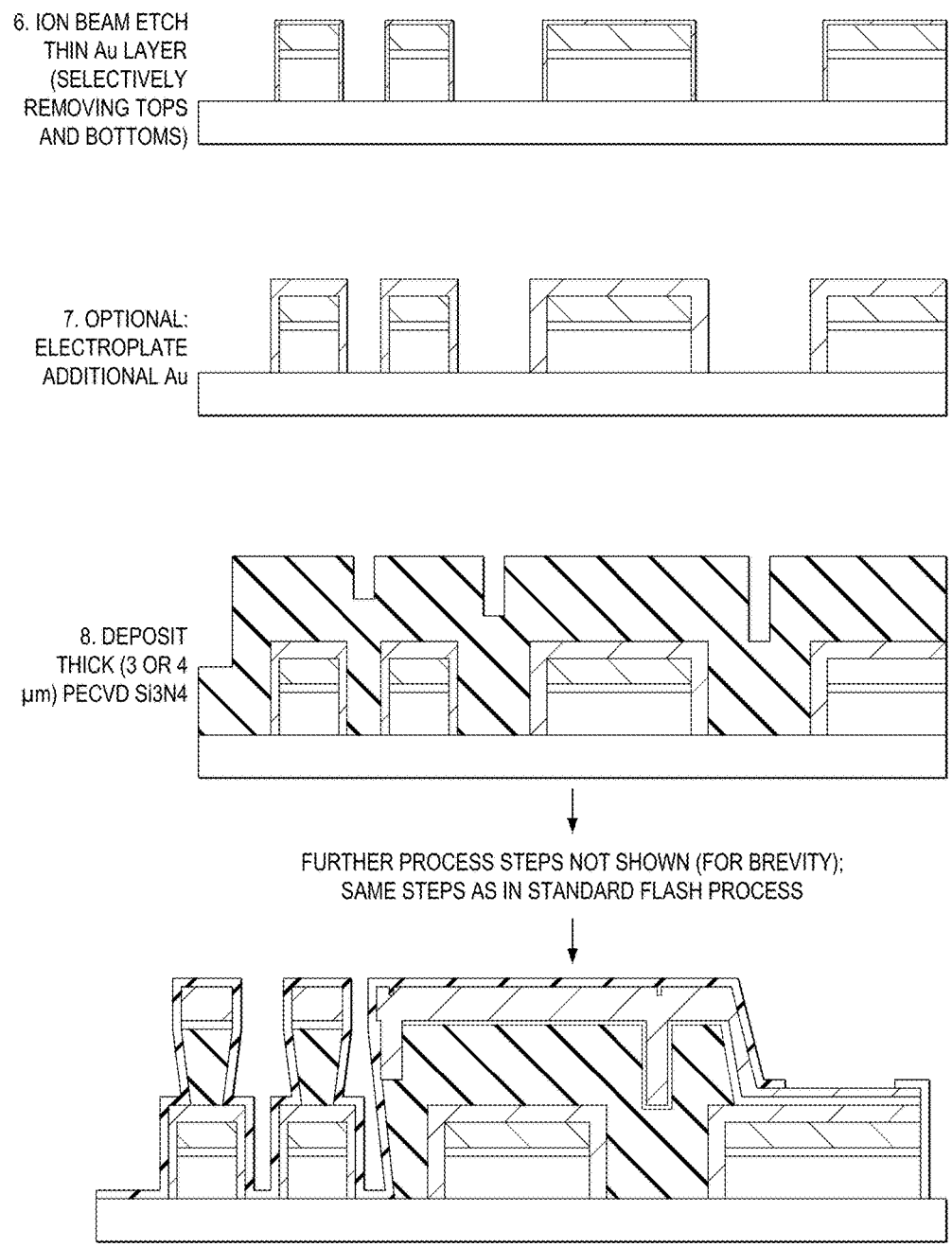

The VRF-FLASh design can be realized using a number of fabrication processes that may be but are not necessarily variations on the existing "FLASh" microfabrication process used to build the sensors. For example, FIGS. 17A and 17B illustrate a schematic cross-sectional view of a thin film microfabrication process sequence used to produce the VRF-FLASh sensor structure 1500 of FIG. 15 according to this disclosure. As illustrated in FIGS. 17A and 17B, the vertical electrodes are realized in a process very similar to the proposed RF-FLASh process (which is itself a relatively minor variation on the FLASh fabrication process), by an additional conformal ALD deposition of a metal such as platinum or gold, thereby coating the sidewalls 1515 of the ridges 1510 with a thin layer. The inventors recognize that, while at present no commercial source of ALD gold or platinum deposition technology exists, such an ALD gold or platinum deposition technology may become commercially available in the future, or potentially another metal, such a iridium, for which ALD deposition technology is available, could be substituted for gold or platinum in this process. This layer is subsequently patterned by an anisotropic direction etch (e.g. ion beam/milling process). Additional or alternative processes are available to perform this patterning, such as a process involving selective sidewall passivation followed by an isotropic etch.

Figure 18:
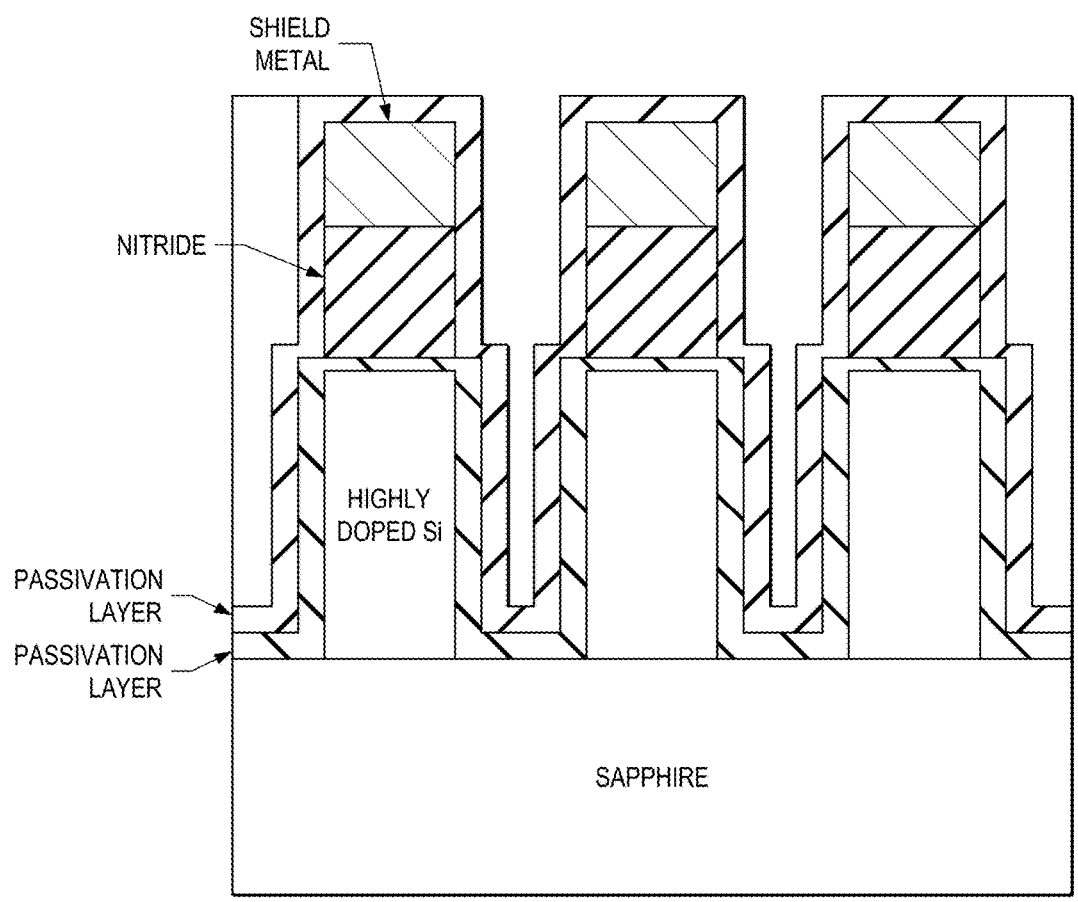

As another example, FIG. 18 illustrates a microfabrication process to produce the VRF-FLASh sensor structure 1500 of FIG. 15 based on a high-aspect ratio etch process according to this disclosure. As shown in FIG. 18, the desired vertical electrode structure is created by a high-aspect ratio (DRIE) etch of highly doped silicon on sapphire (or other insulating substrate), a process well-known in the MEMS field, popular to realize, e.g., comb drive sensors and actuators. Only the portion of active sensing area is depicted.

Figure 19:
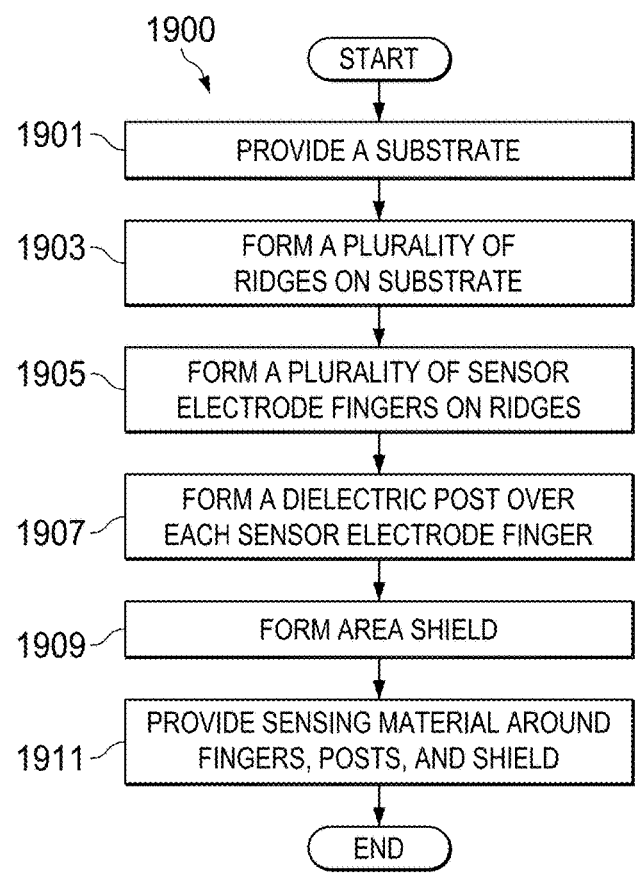
FIG. 19 illustrates an example method for fabricating a shielded sensing structure according to this disclosure.

FIG. 19 illustrates an example method 1900 for fabricating a shielded sensing structure according to this disclosure. For ease of explanation, the method 1900 is described as being performed to fabricate one or more of the sensing structures described herein. However, the method 1900 could be used for any suitable shielded sensing structure.

At step 1901, a substrate is provided. This can include, for example, providing one of the substrates 304, 804, 904, 1404, 1504 using any one or more of the processes described above.

At step 1903, a plurality of ridges are formed on a top surface of the substrate. This can include, for example, forming the ridges 1410, 1510 using any one or more of the processes described above. In particular embodiments, this can include, for example, depositing one or more layers and then etching the layers to form the ridges. In some embodiments, the etching may occur later, such as after steps 1905-1909.

At step 1905, a plurality of parallel interdigitated sensor electrode fingers are formed on the ridges. This can include, for example, forming the electrode fingers 302, 802, 902, 1402, 1502 using any one or more of the processes described above. Each ridge elevates the corresponding sensor electrode finger from the top surface of the substrate. In some embodiments, the ridges are formed by anisotropic reactive ion etching using the sensor electrode fingers as a mask. In some embodiments, each ridge includes vertical sidewalls that are coated with a conductive material that is formed integrally with the corresponding sensor electrode finger.

At step 1907, a dielectric post is formed over each of the sensor electrode fingers. This can include, for example, forming the dielectric posts 316, 816, 916, 1416, 1516 using any one or more of the processes described above.

At step 1909, an area shield is formed, such that a portion of the area shield is disposed over each dielectric post. This can include, for example, forming the area shield 312, 812, 912, 1412, 1512 using any one or more of the processes described above.

At step 1911, a sensing material is provided in gaps formed by surfaces of the sensor electrode fingers, the dielectric posts, and the area shield. This can include, for example, providing the sensing material 401, 801, 901, 1401, 1501 using any one or more of the processes described above.

Although FIG. 19 illustrates one example of a method 1900 for fabricating a shielded sensing structure, various changes may be made to FIG. 19. For example, while shown as a series of steps, various steps shown in FIG. 19 could overlap, occur in parallel, occur in a different order, or occur multiple times. Moreover, some steps could be combined or removed and additional steps could be added according to particular needs.

The embodiments described above offer, for the same sensing materials and electrode sizes, significant improvements in chemical sensitivity of the sensors, as well as reduced parasitic substrate capacitance and other benefits that contribute to enhanced sensor performance. In contrast to the aforementioned implementations with co-planar guard or shield electrodes, the electric field confinement and immunity to external fields and external charges in accordance with this disclosure is advantageous. Also, compared to a solution where the thickness of sensing material would be increased, the disclosed embodiments enable the use of much thinner sensing material layers and hence faster response times and greater ease of fabrication (e.g., thickness uniformity, material homogeneity, and the like).

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The terms "transmit" and "receive," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims is intended to invoke 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," or "controller" within a claim is understood and intended to refer to structures known to those skilled in the relevant art, as further modified or enhanced by the features of the claims themselves, and is not intended to invoke 35 U.S.C. § 112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A sensor apparatus comprising:
 a substrate;
 a plurality of parallel interdigitated sensor electrode fingers disposed over the substrate;
 a peripheral shield disposed over at least some of a periphery of the substrate; and
 a sensing material disposed in gaps formed by surfaces of the sensor electrode fingers and the peripheral shield.

2. The sensor apparatus of claim 1, wherein the sensor electrode fingers are disposed directly on a top surface of the substrate.

3. The sensor apparatus of claim 1, further comprising:
 a dielectric post disposed over each of the sensor electrode fingers, wherein:
  the peripheral shield forms part of a shielding system that further includes an area shield, wherein a portion of the area shield is disposed over each dielectric post,
  the peripheral shield is coplanar with the area shield, and
  the shielding system is electrically insulated from the sensor electrode fingers.

4. The sensor apparatus of claim 3, wherein the area shield comprises a plurality of parallel lines that are physically and electrically connected and are disposed in a plane over the dielectric posts.

5. The sensor apparatus of claim 4, wherein the lines of the area shield are collinear with or perpendicular to the dielectric posts.

6. The sensor apparatus of claim 3, wherein the sensor electrode fingers are formed as part of an M1 metallization layer over the substrate, and the area shield is formed as part of an M2 metallization layer over the M1 metallization layer.

7. The sensor apparatus of claim 1, wherein each sensor electrode finger is disposed on a ridge that is formed on a top surface of the substrate, each ridge elevating the corresponding sensor electrode finger from the top surface of the substrate.

8. The sensor apparatus of claim 7, wherein the ridges are formed by anisotropic reactive ion etching using the sensor electrode fingers as a mask.

9. The sensor apparatus of claim 7, wherein a vertical height of each ridge is greater than a lateral distance between adjacent ridges.

10. The sensor apparatus of claim 7, wherein each ridge includes vertical sidewalls that are coated with a conductive material that is formed integrally with the corresponding sensor electrode finger.

11. A method for fabricating a sensing structure comprising:
 providing a substrate;
 forming a plurality of parallel interdigitated sensor electrode fingers over the substrate;
 forming a peripheral shield over at least some of a periphery of the substrate; and
 providing a sensing material in gaps formed by surfaces of the sensor electrode fingers and the peripheral shield.

12. The method of claim 11, wherein the sensor electrode fingers are formed directly on a top surface of the substrate.

13. The method of claim 11, further comprising:
 forming a dielectric post over each of the sensor electrode fingers, wherein:
  the peripheral shield is formed as part of a shielding system that further includes an area shield, wherein a portion of the area shield is disposed over each dielectric post,
  the peripheral shield is coplanar with the area shield, and
  the shielding system is electrically insulated from the sensor electrode fingers.

14. The method of claim 13, wherein the area shield comprises a plurality of parallel lines that are physically and electrically connected and are disposed in a plane over the dielectric posts.

15. The method of claim 14, wherein the lines of the area shield are collinear with or perpendicular to the dielectric posts.

16. The method of claim 13, wherein the sensor electrode fingers are formed by forming an M1 metallization layer over the substrate, and the area shield is formed by forming an M2 metallization layer over the M1 metallization layer.

17. The method of claim 11, further comprising:
 before forming the sensor electrode fingers over the substrate, forming a plurality of ridges on a top surface of the substrate, wherein each sensor electrode finger is formed on a corresponding one of the ridges, each ridge elevating the corresponding sensor electrode finger from the top surface of the substrate.

18. The method of claim 17, wherein the ridges are formed by anisotropic reactive ion etching using the sensor electrode fingers as a mask.

19. The method of claim 17, wherein a vertical height of each ridge is greater than a lateral distance between adjacent ridges.

20. The method of claim 17, wherein each ridge includes vertical sidewalls that are coated with a conductive material that is formed integrally with the corresponding sensor electrode finger.

* * * * *